United States Patent
Gao et al.

(10) Patent No.: US 11,667,618 B2
(45) Date of Patent: Jun. 6, 2023

(54) AZULENE RING-CONTAINING COMPOUND, ITS USE, AND AN ORGANIC PHOTOELECTRIC DEVICE INCLUDING THE SAME

(71) Applicants: WUHAN TIANMA MICROELECTRONICS CO., LTD., Wuhan (CN); WUHAN TIANMA MICROELECTRONICS CO., LTD. SHANGHAI BRANCH, Shanghai (CN)

(72) Inventors: Tiezhen Gao, Shanghai (CN); Wei Gao, Shanghai (CN); Jinghua Niu, Shanghai (CN)

(73) Assignee: Wuhan Tianma Micro-Electronics Co., Ltd., Wuhan (CN)

( * ) Notice: Subject to any disclaimer, the term of this patent is extended or adjusted under 35 U.S.C. 154(b) by 323 days.

(21) Appl. No.: 16/875,606

(22) Filed: May 15, 2020

(65) Prior Publication Data

US 2020/0377467 A1    Dec. 3, 2020

(30) Foreign Application Priority Data

May 31, 2019 (CN) .......................... 201910472989.9

(51) Int. Cl.

| | |
|---|---|
| C07D 307/93 | (2006.01) |
| H01L 51/00 | (2006.01) |
| C07D 333/78 | (2006.01) |
| C07D 221/18 | (2006.01) |
| C07D 471/04 | (2006.01) |
| C07D 487/04 | (2006.01) |
| C07D 209/82 | (2006.01) |
| C07D 491/048 | (2006.01) |
| C07D 495/04 | (2006.01) |
| C07D 403/14 | (2006.01) |
| C07D 265/38 | (2006.01) |
| C07D 409/04 | (2006.01) |
| C07D 279/18 | (2006.01) |
| C07D 221/06 | (2006.01) |
| C07C 211/19 | (2006.01) |

(52) U.S. Cl.
CPC .......... *C07D 307/93* (2013.01); *C07C 211/19* (2013.01); *C07D 209/82* (2013.01); *C07D 221/06* (2013.01); *C07D 221/18* (2013.01); *C07D 265/38* (2013.01); *C07D 279/18* (2013.01); *C07D 333/78* (2013.01); *C07D 403/14* (2013.01); *C07D 409/04* (2013.01); *C07D 471/04* (2013.01); *C07D 487/04* (2013.01); *C07D 491/048* (2013.01); *C07D 495/04* (2013.01); *H10K 85/40* (2023.02); *H10K 85/622* (2023.02); *H10K 85/633* (2023.02); *H10K 85/636* (2023.02); *H10K 85/6572* (2023.02); *H10K 85/6574* (2023.02); *H10K 85/6576* (2023.02); *C07C 2603/40* (2017.05); *H10K 50/11* (2023.02)

(58) Field of Classification Search
None
See application file for complete search history.

(56) References Cited

PUBLICATIONS

Grants. Hackh's Chemical Dictionary (5th Ed. 1987) at p. 148.*
Kitamori et al., Synthesis of a Polycyclic π-Conjugated System Containing an Azulene Unit by the Flash Vacuum Pyrolytic Method. III. Synthesis and Properties of 4-Hydroxy-3H-cyclopent[a]azulen-3-one. Bulletin of the Chemical Society of Japan, 1992, 65, 3282-3287.*

* cited by examiner

*Primary Examiner* — Po-Chih Chen
(74) *Attorney, Agent, or Firm* — von Briesen & Roper, s.c.

(57) ABSTRACT

The present disclosure provides an azulene ring-containing compound, its use, and an organic photoelectric device including the same. The azulene ring-containing compound is a compound comprising a structure of Formula I. The organic photoelectric device includes an anode, a cathode, and one or more organic thin film layers located between the anode and the cathode; and at least one of the organic thin film layers contains the above-mentioned azulene ring-containing compound comprising the structure of Formula I. The azulene ring-containing compound provided by the present disclosure has an energy level difference $\Delta Est \leq 0.3$ eV between the lowest singlet state $S_1$ and the lowest triplet state $T_1$, and has a light-emitting mechanism of a thermally activated delayed fluorescent material, and can be used as a thermally activated delayed fluorescent material for organic photoelectric device, so that the light-emitting efficiency of the device is improved.

19 Claims, 1 Drawing Sheet

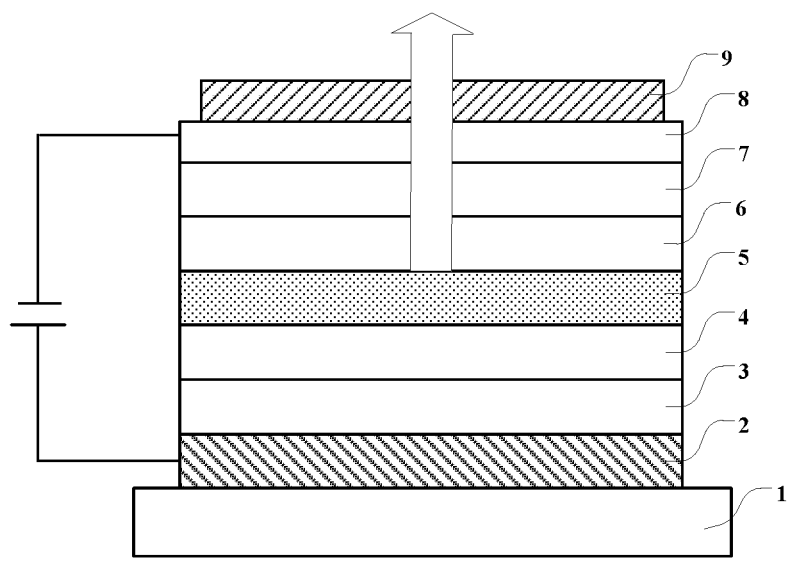

AZULENE RING-CONTAINING COMPOUND, ITS USE, AND AN ORGANIC PHOTOELECTRIC DEVICE INCLUDING THE SAME

CROSS-REFERENCE TO RELATED APPLICATIONS

The application claims the benefit of the earlier filing date of Chinese Patent Application No. 201910472989.9, filed on May 31, 2019 to the China National Intellectual Property Administration, the contents of which are incorporated by reference herein in its entirety.

TECHNICAL FIELD

The present disclosure belongs to the technical field of organic light-emitting materials, and relates to a thermally activated delayed fluorescent material, in particular to an azulene ring-containing compound, its use, and an organic photoelectric device including the same.

BACKGROUND

An organic light-emitting diode (OLED) is a kind of light-emitting device based on organic light-emitting materials which has advantages such as wide viewing angle, ultra-thin, fast response, high light-emitting efficiency, and realizable flexible display, thus it is regarded as a globally recognized next-generation mainstream display after liquid crystal.

According to light-emitting mechanism, there are mainly four types of materials can be used in an OLED light-emitting layer: fluorescent materials, phosphorescent materials, triplet-triplet annihilation (TTA) materials, and thermally activated delayed fluorescent (TADF) materials.

According to spin statistics, a ratio of singlet excitons to triplet excitons in excitons is 1:3, so that the maximum internal quantum yield of fluorescent materials does not exceed 25%. According to the Lambertian luminous mode, light extraction efficiency is about 20%, so that the external quantum efficiency (EQE) of OLED devices based on fluorescent materials does not exceed 5%.

Due to heavy atom effect, intramolecular intersystem crossing in phosphorescent materials can be strengthened through spin coupling and 75% of triplet excitons can be directly used to achieve co-participated emission of the lowest singlet state ($S_1$) excitons and the lowest triplet state ($T_1$) excitons at room temperature, so that the theoretical maximum internal quantum yield can reach 100%. Therefore, EQE of OLED devices based on phosphorescent materials can reach 20%. However, phosphorescent materials are substantially complexes of heavy metals such as Ir, Pt, Os, Re, and Ru such that its production cost is high, which is not conducive to large-scale production. Moreover, under high current density, there is a serious efficiency roll-off phenomenon of phosphorescent materials, so that stability of a phosphorescent OLED device is not good.

TTA materials can use two adjacent triplet excitons to recombine to generate one singlet excited state molecule at a higher energy level and one ground state molecule, but two triplet excitons can only generate one singlet exciton, thus the theoretical maximum internal quantum yield of TTA materials can only reach 62.5%. At the same time, in order to prevent a greater efficiency roll-off phenomenon, concentration of triplet excitons in light emission process of TTA materials needs to be adjusted.

TADF materials have smaller singlet and triplet energy level differences. $T_1$ state excitons can switch to $S_1$ state by absorbing ambient heat through reverse intersystem crossing, 75% of triplet state excitons and 25% of single state excitons can be used at the same time, and the theoretical maximum internal quantum yield can reach 100%. TADF materials are mainly organic compounds which do not require rare metal elements, thus they have low production costs and can be chemically modified by various methods.

However, less TADF materials have been found so far, and there is still a need to develop new TADF materials that can be used in OLED devices.

SUMMARY

In view of shortcomings of the related techniques, an object of the present disclosure is to provide an azulene ring-containing compound, its use, and an organic photoelectric device including the same.

To achieve this object, the present disclosure adopts the following technical solutions:

In a first aspect, the present disclosure provides an azulene ring-containing compound, which is a compound comprising the structure of Formula I:

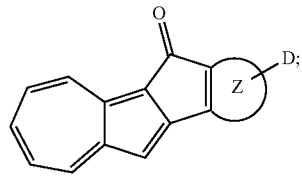

Formula I

In Formula I, the Z ring

represents an unsaturated five-membered ring or an unsaturated six-membered ring, and D represents an electron-donating group.

In a second aspect, the present disclosure provides a use of the above-mentioned azulene ring-containing compound. The azulene ring-containing compound is used as a thermally activated delayed fluorescent material.

In a third aspect, the present disclosure provides an organic photoelectric device including an anode, a cathode, and one or more organic thin film layers located between the anode and the cathode. At least one of the organic thin film layers contains the azulene ring-containing compound provided by the first aspect of the present disclosure.

Compared with the related techniques, the present disclosure has the following beneficial effects:

In the present disclosure, the five-membered ring site of azulene is functionally modified with an unsaturated five-membered ring or an unsaturated six-membered ring. The formed azulene-unsaturated five-membered ring material and azulene-unsaturated six-membered ring material combine the excellent chemical and physical properties of azulene ring and unsaturated aromatic rings. By incorporating the azulene-unsaturated five-membered ring or the azulene-unsaturated six-membered ring as an electron acceptor with an electron donating group, the formed compound has an energy level difference between the lowest singlet state $S_1$ and the lowest triplet state $T_1$ below 0.3 eV, ie. $\Delta E_{st} \leq 0.3$ eV, thus $T_1$ state excitons can convert to the $S_1$ state by reverse intersystem crossing. The formed compound has a light-emitting mechanism of TADF materials, and thus can be used in organic optoelectronic devices to improve light-emitting efficiency.

BRIEF DESCRIPTION OF THE DRAWINGS

FIG. 1 is a structural schematic diagram of an organic light-emitting device provided by an embodiment of the present disclosure; wherein 1 is a glass substrate, 2 is an ITO anode, 3 is a first hole transport layer, 4 is a second hole transport layer, 5 is a light-emitting layer, 6 is a first electron transport layer, 7 is a second electron transport layer, 8 is a cathode and 9 is a cathode cover layer.

DETAILED DESCRIPTION

The technical solution of the present disclosure will be further described below by way of specific embodiments in combination with accompanying drawings. It will be apparent to those skilled in the art that the specific embodiments are merely illustrations of the present disclosure and should not be construed as specific limitations to the present disclosure.

In a first aspect, the present disclosure provides an azulene ring-containing compound, which is a compound comprising the structure of Formula I:

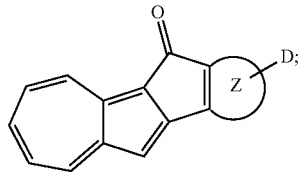

Formula I

In Formula I, Z ring

represents an unsaturated five-membered ring or an unsaturated six-membered ring, and D represents an electron-donating group.

Azulene molecule can be regarded as a combination of positively charged cycloheptatriene and negatively charged cyclopentadiene, thus it has a larger dipole moment (1.08 D), so that an azulene derivative organic material has a good charge transfer performance and electron donating performance. Since an azulene derivative organic material usually has good stability and unique electrical, optical, redox, and self-assembly properties, it is an important candidate of organic optoelectronic materials.

In the present disclosure, the five-membered ring site of azulene is functionally modified with an unsaturated five-membered ring or an unsaturated six-membered ring. The formed azulene-unsaturated five-membered ring material and the azulene-unsaturated six-membered ring material combine the excellent chemical and physical properties of azulene ring and unsaturated aromatic rings.

By incorporating the azulene-unsaturated five-membered ring or the azulene-unsaturated six-membered ring as an electron acceptor with an electron donating group, the formed compound has a smaller energy level difference between the lowest singlet state $S_1$ and the lowest triplet state $T_1$, thus $T_1$ state excitons can convert to the $S_1$ state by reverse intersystem crossing. The formed compound has a light-emitting mechanism of TADF materials.

In one embodiment of the present disclosure, Z ring in Formula I is a benzene ring, a thiophene ring, a furan ring, or a pyridine ring.

In one embodiment of the present disclosure, the azulene ring-containing compound is a compound comprising the structure of Formula II:

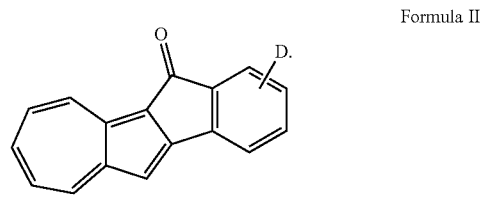

Formula II

In one embodiment of the present disclosure, the azulene ring-containing compound is a compound comprising the structure of Formula III:

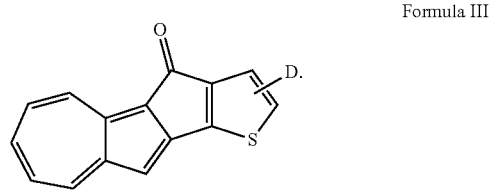

Formula III

In one embodiment of the present disclosure, the azulene ring-containing compound is a compound comprising the structure of Formula IV:

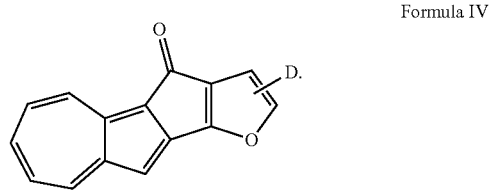

Formula IV

In one embodiment of the present disclosure, the azulene ring-containing compound is a compound comprising the structure of Formula V:

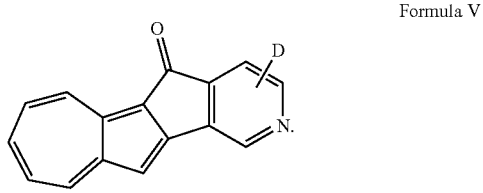

Formula V

In one embodiment of the present disclosure, D represents an electron-donating group containing nitrogen.

In one embodiment of the present disclosure, D is selected from any one of the following groups:

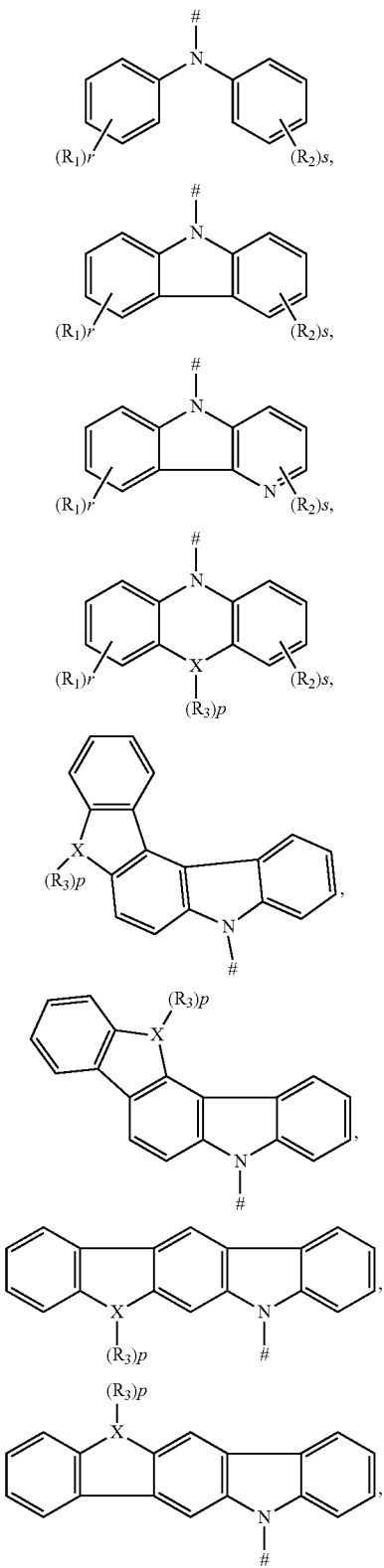

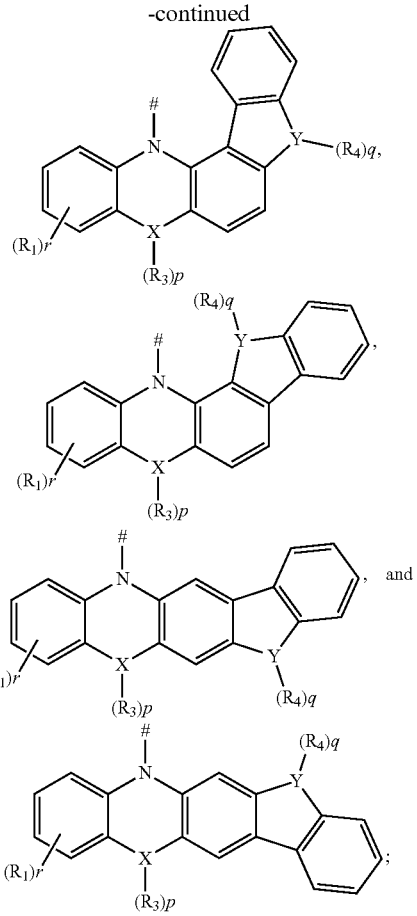

-continued wherein X and Y each is independently selected from one of a carbon atom, a nitrogen atom, an oxygen atom, a sulfur atom, and a silicon atom.

$R_1$ and $R_2$ each is independently selected from any one of a substituted or unsubstituted alkyl group having 1 to 20 (e.g., 1, 2, 3, 5, 6, 8, 10, 12, 13, 15, 16, 18 or 20) carbon atoms, a substituted or unsubstituted alkoxy group having 1 to 20 (e.g., 1, 2, 3, 5, 6, 8, 10, 12, 13, 15, 16, 18 or 20) carbon atoms, a substituted or unsubstituted phenyl group, a substituted or unsubstituted carbazolyl, a substituted or unsubstituted diphenylamino; r and s each is independently 0, 1, 2 or 3.

$R_3$ and $R_4$ each is independently selected from any one of hydrogen atom, a substituted or unsubstituted alkyl group having 1 to 20 (e.g., 1, 2, 3, 5, 6, 8, 10, 12, 13, 15, 16, 18 or 20) carbon atoms, a substituted or unsubstituted alkoxy group having 1 to 20 (e.g., 1, 2, 3, 5, 6, 8, 10, 12, 13, 15, 16, 18 or 20) carbon atoms, a substituted or unsubstituted phenyl group, a substituted or unsubstituted carbazolyl, a substituted or unsubstituted diphenylamino; p and q each is independently 0, 1 or 2.

# represents a linking site of a group,

When X or Y is a carbon atom or a silicon atom, p or q is 2;

When X or Y is a nitrogen atom, p or q is 1; and

When X or Y is an oxygen atom or a sulfur atom, p or q is 0.

In one embodiment of the present disclosure, the substituted or unsubstituted phenyl group has a structural formula of

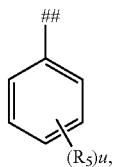

the substituted or unsubstituted carbazolyl group has a structural formula of

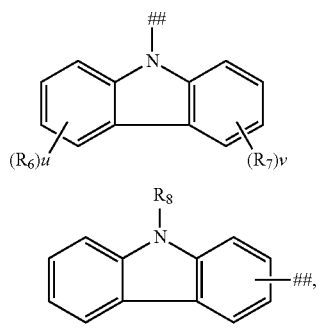

and the substituted or unsubstituted diphenylamino group has a structural formula of

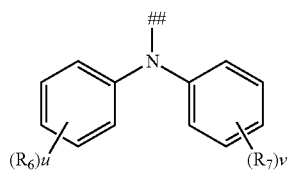
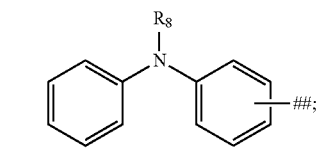

wherein $R_5$, $R_6$, $R_7$ and $R_8$ each is independently selected from any one of an alkyl group having 1 to 20 (e.g., 1, 2, 3, 5, 6, 8, 10, 12, 13, 15, 16, 18 or 20) carbon atoms, an alkoxy group having 1 to 20 (e.g., 1, 2, 3, 5, 6, 8, 10, 12, 13, 15, 16, 18 or 20) carbon atoms, and a phenyl group;

u and v each is independently 0, 1, 2 or 3; and represents a linking site of a group.

In one embodiment of the present disclosure, D is selected from any one of the following groups:

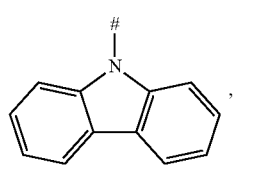
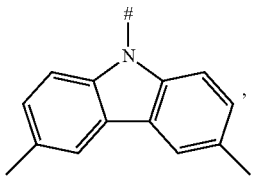

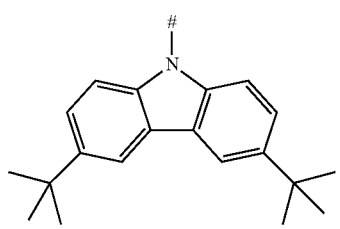

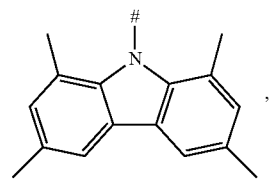

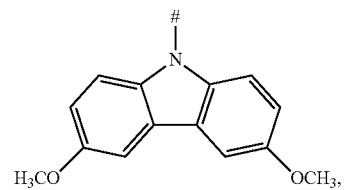

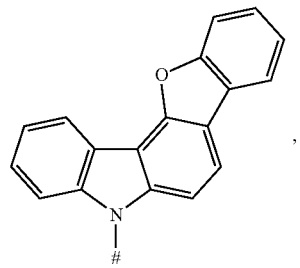

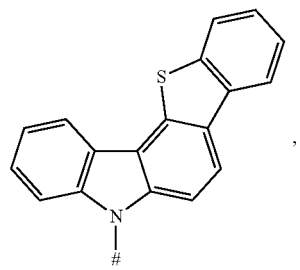

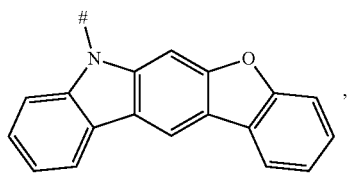

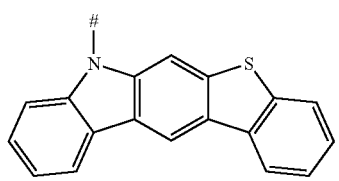

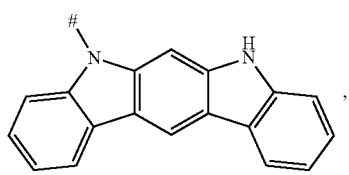

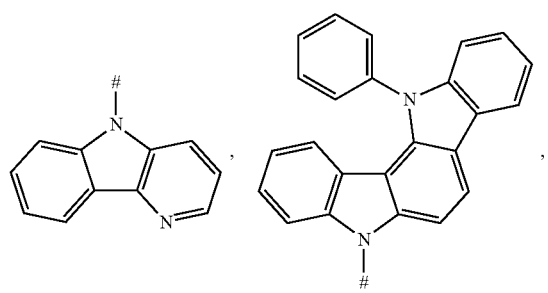
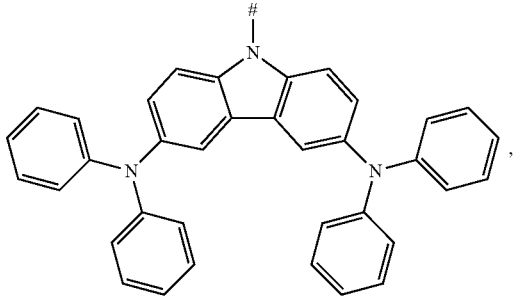
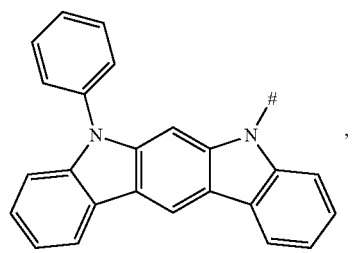
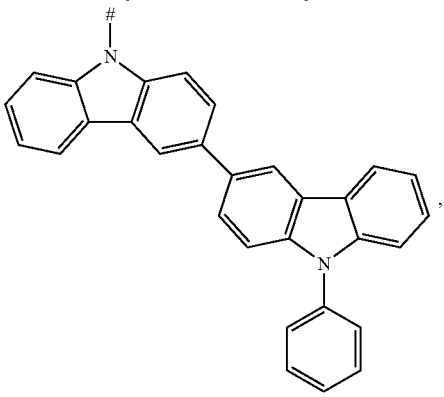
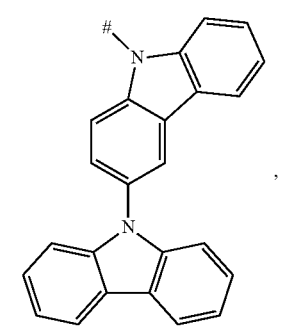
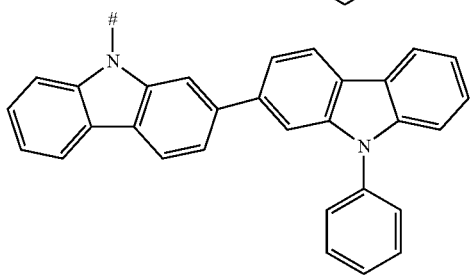
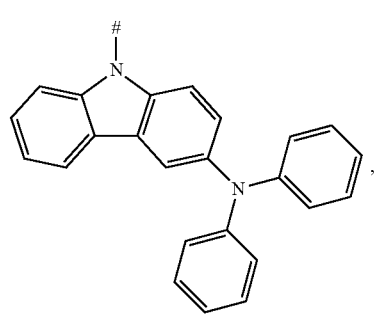
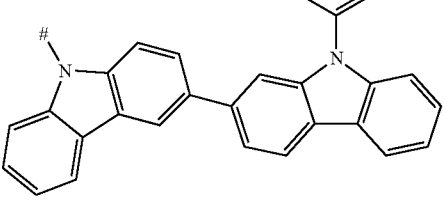
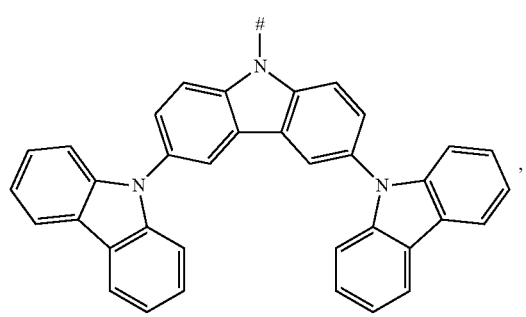
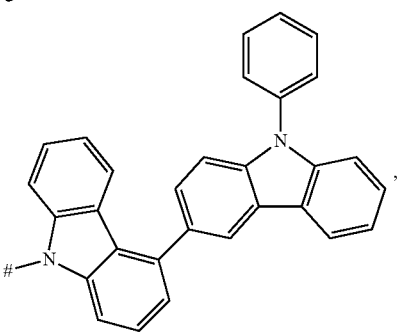
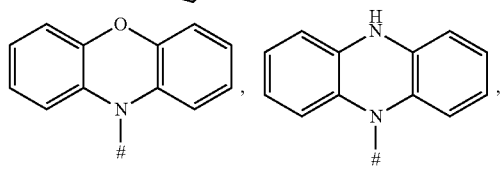

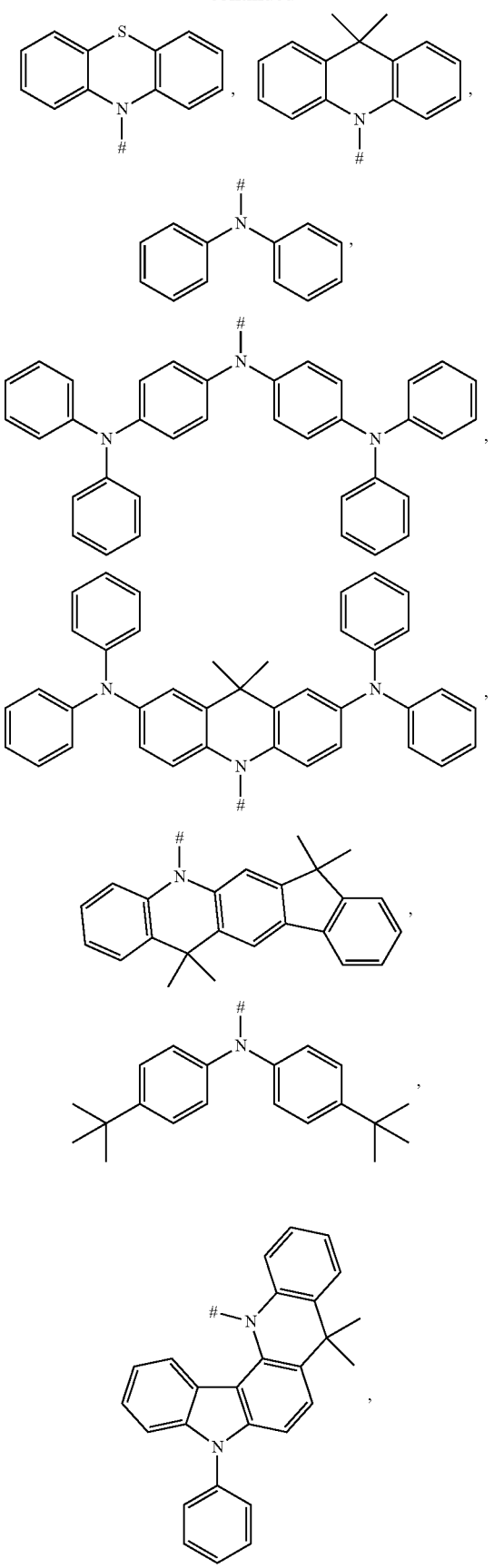
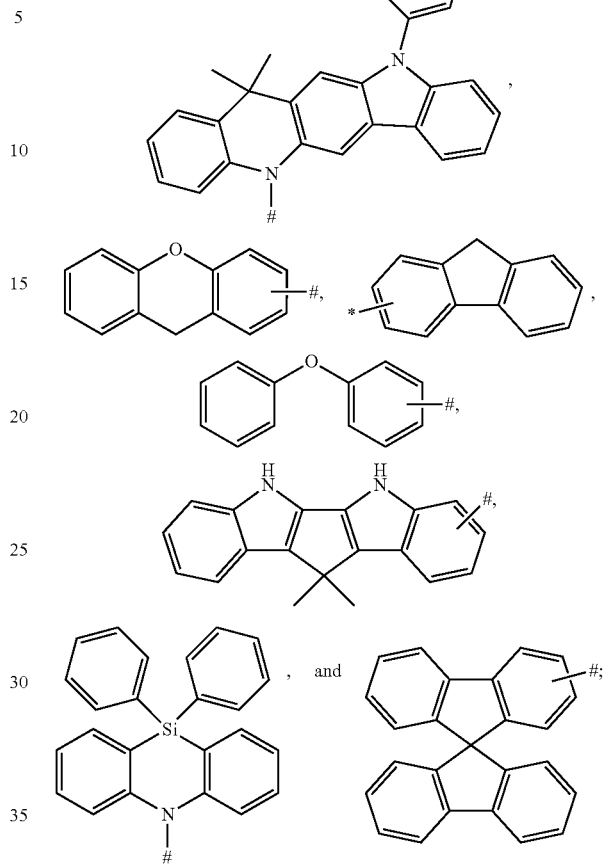
wherein # represents a linking site of a group.
In one embodiment of the present disclosure, the azulene ring-containing compound is a compound comprising any one of the following structures:
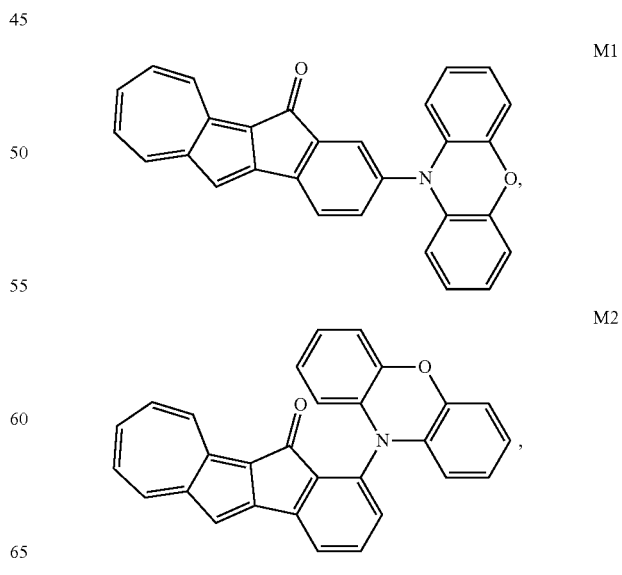

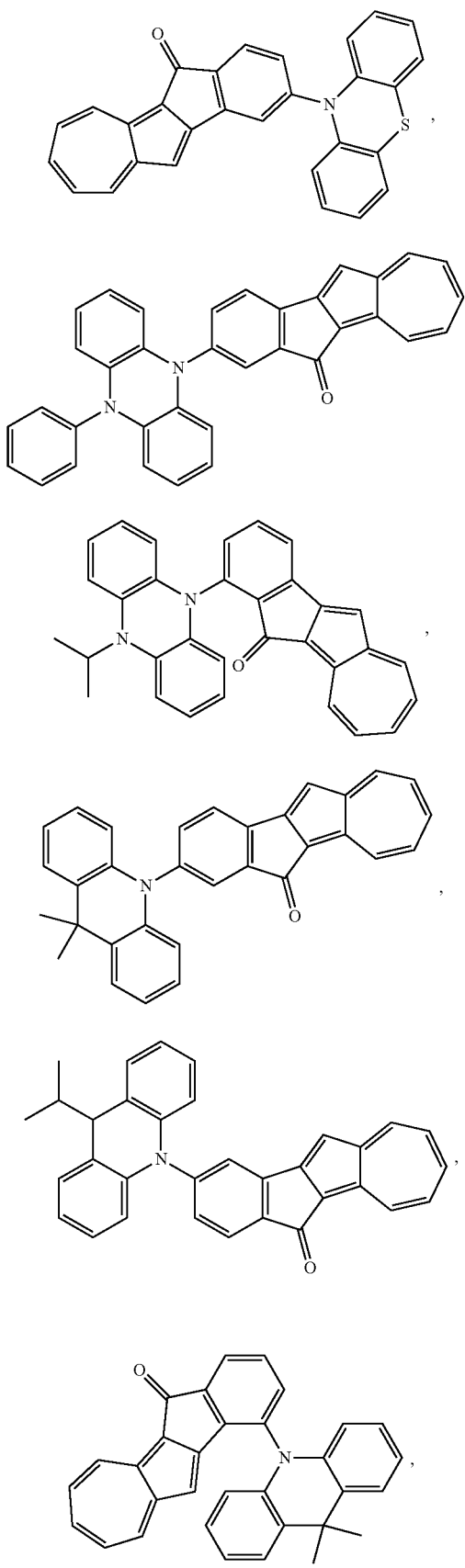
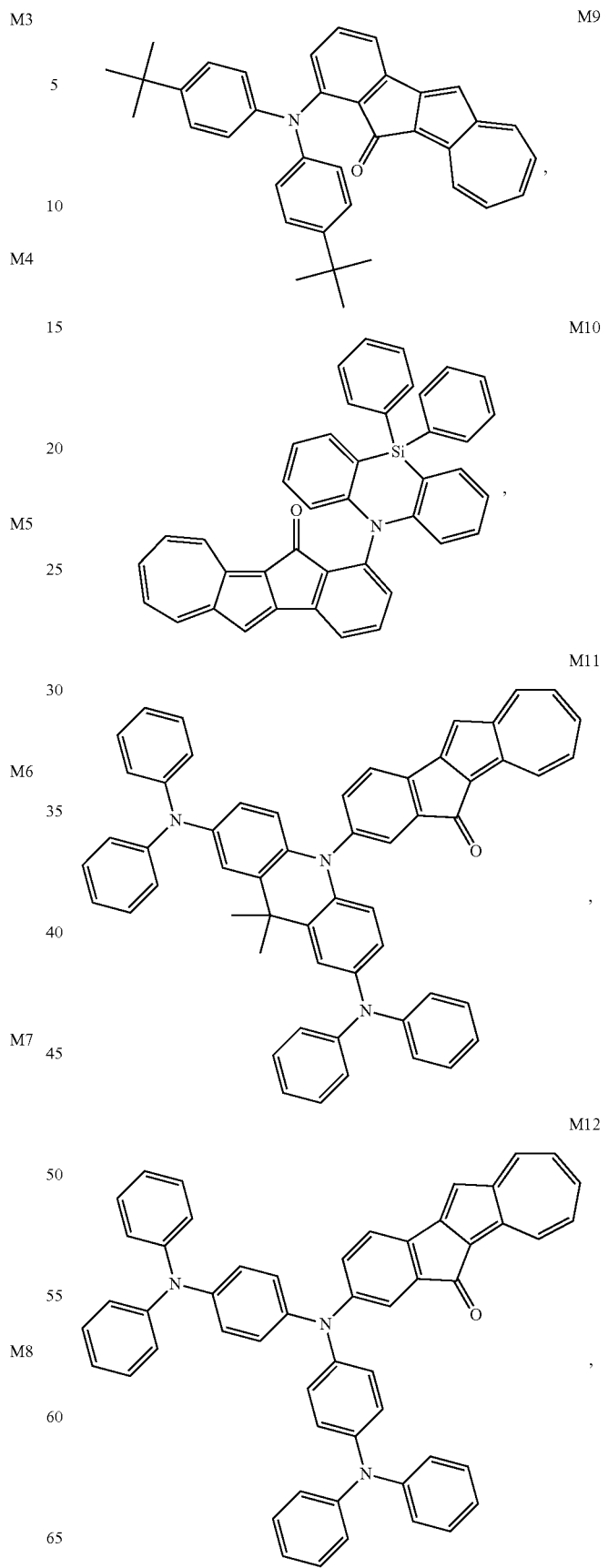

-continued
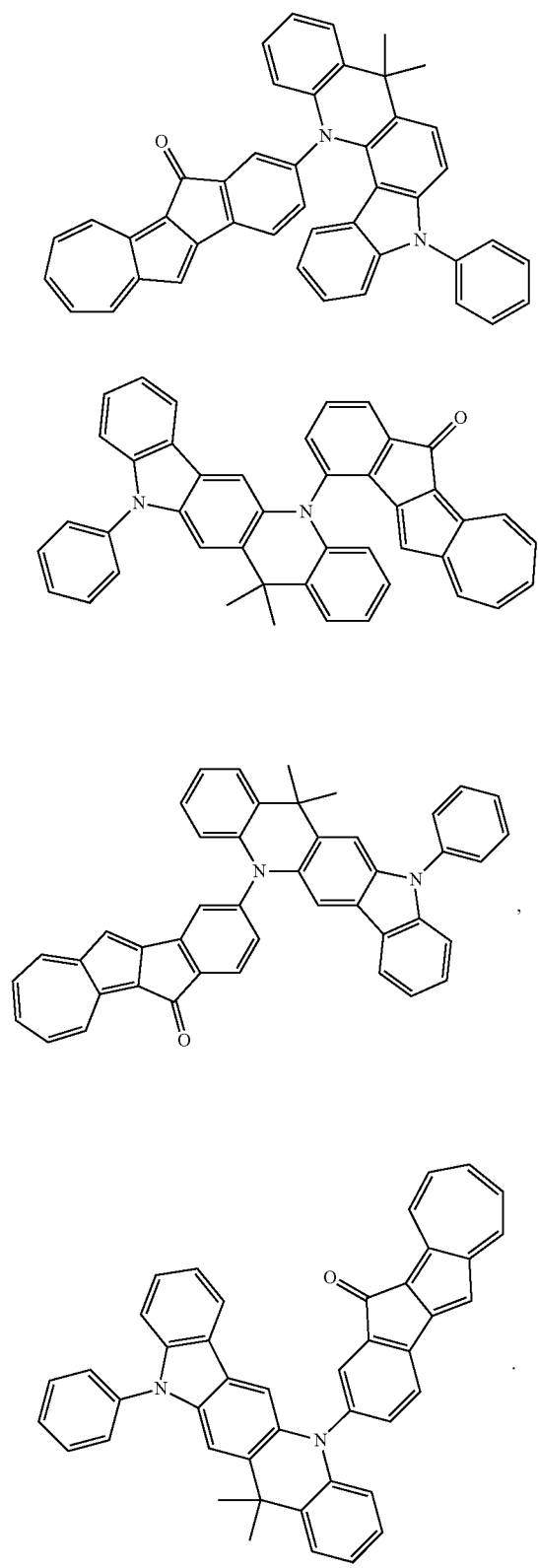
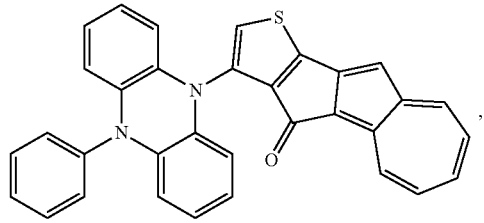
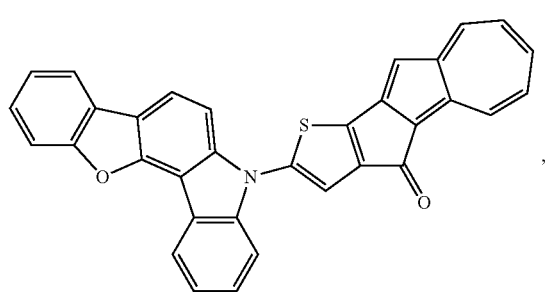
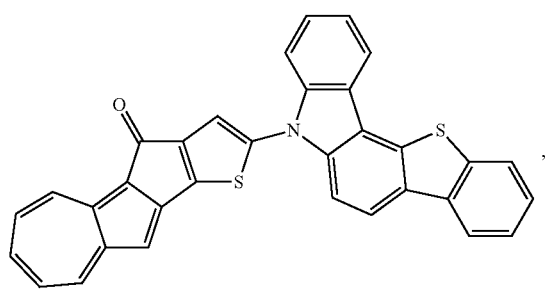
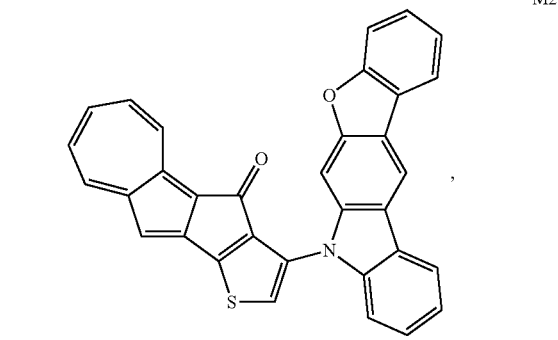
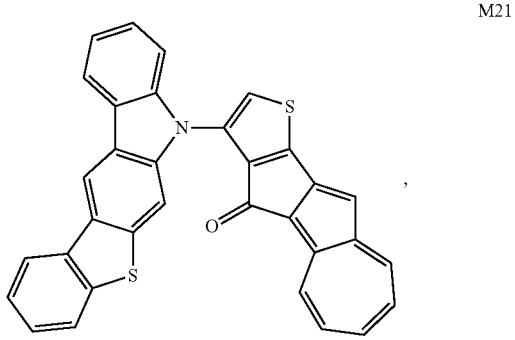
In one embodiment of the present disclosure, the azulene ring-containing compound is a compound comprising any one of the following structures:

M22
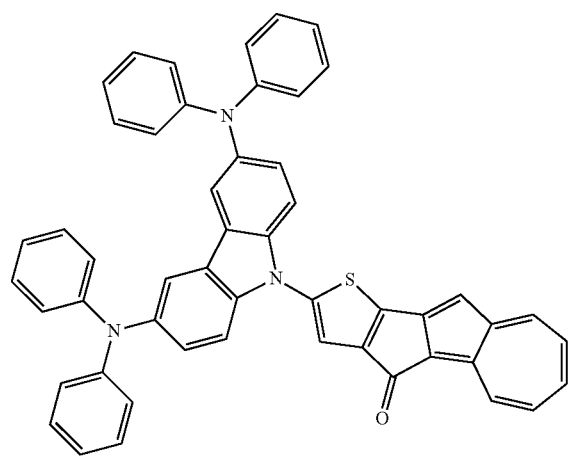
M23
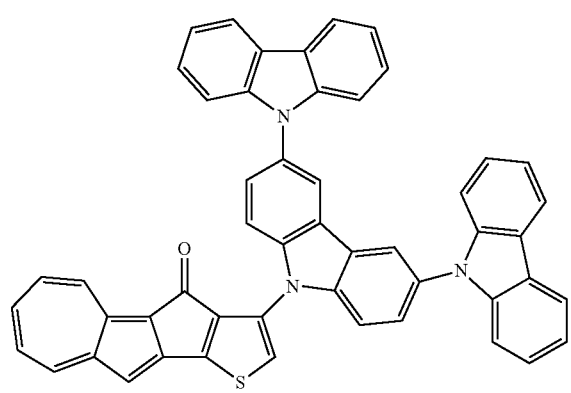
M24
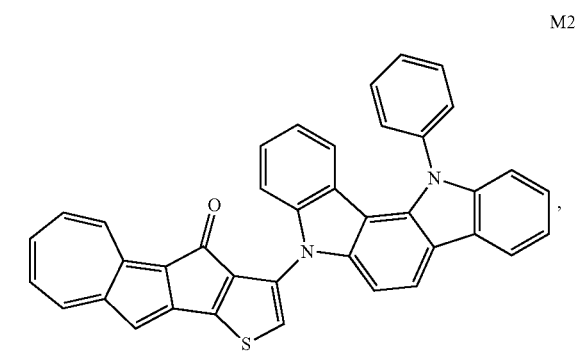
M25
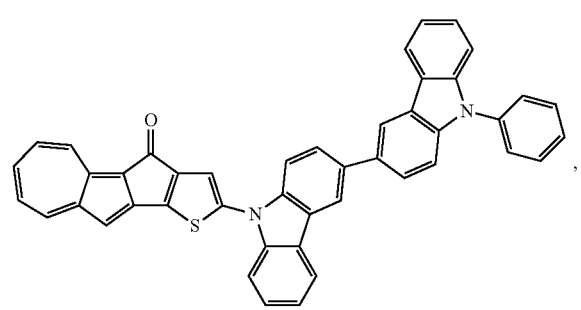
M26
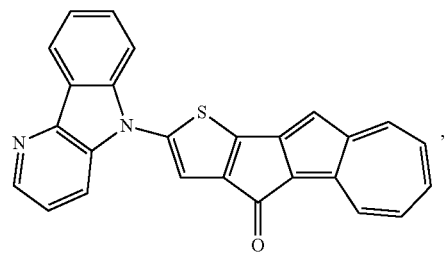
M27
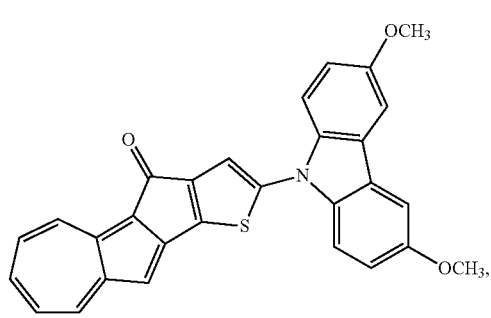
M28
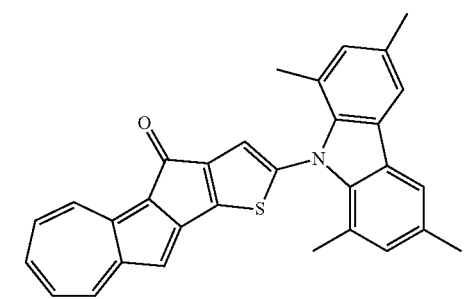
M29
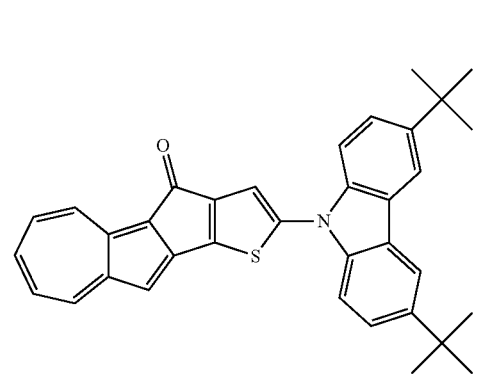
M30
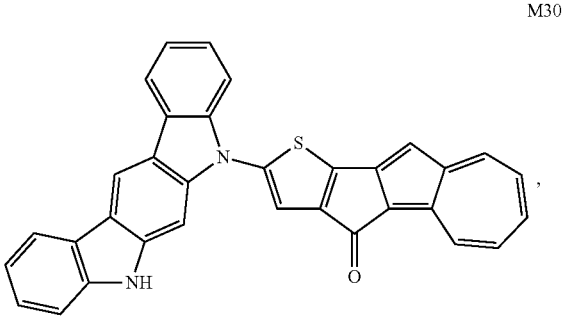

-continued
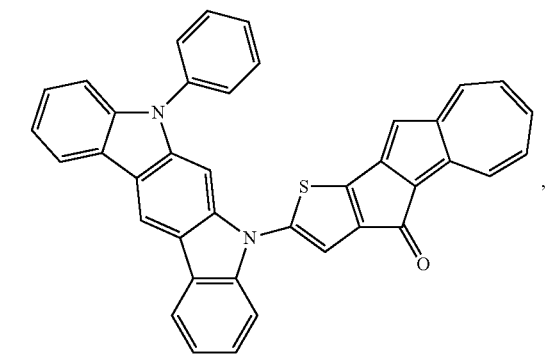
M31
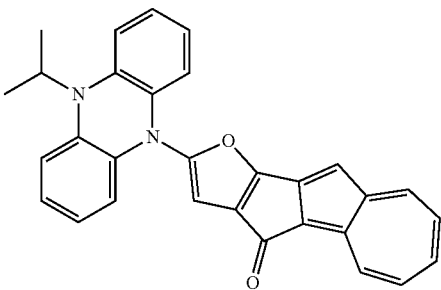
M35
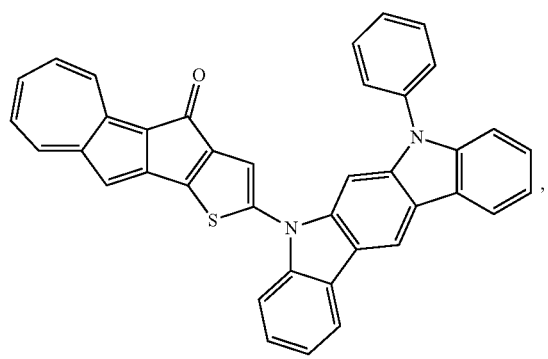
M32
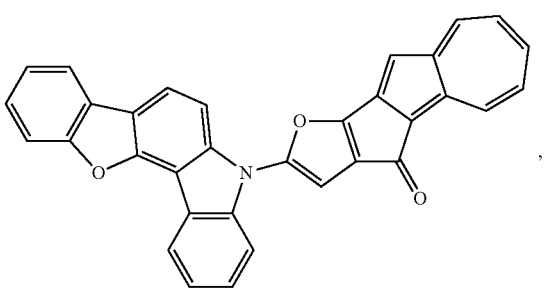
M36
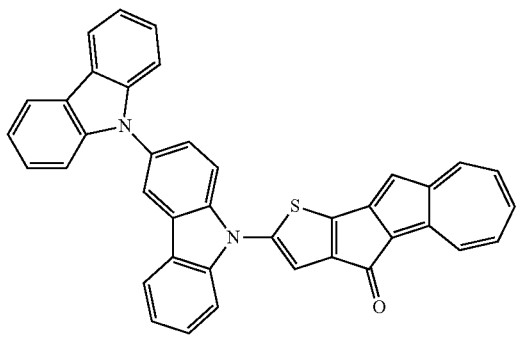
M33
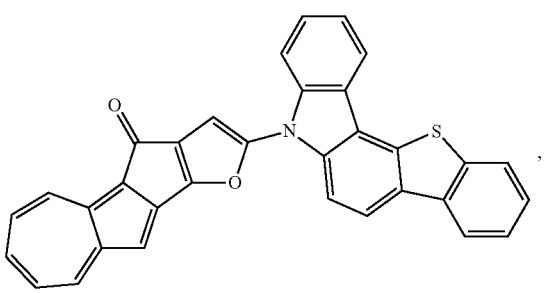
M37
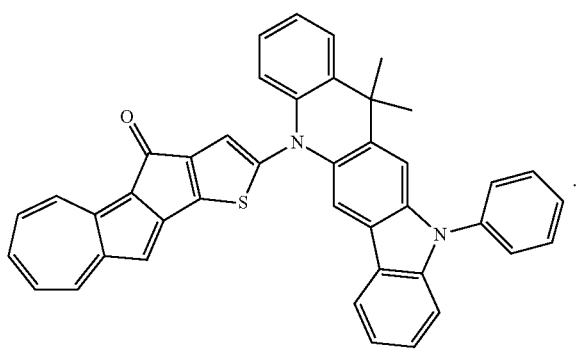
M34
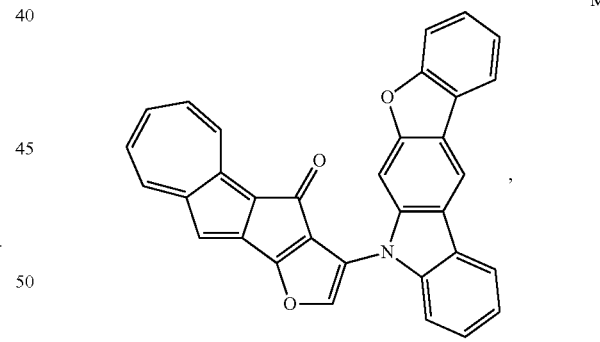
M38
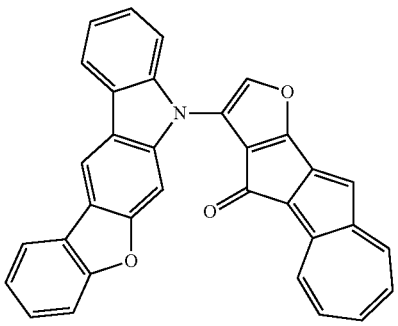
M39
In one embodiment of the present disclosure, the azulene ring-containing compound is a compound comprising any one of the following structures:

M40
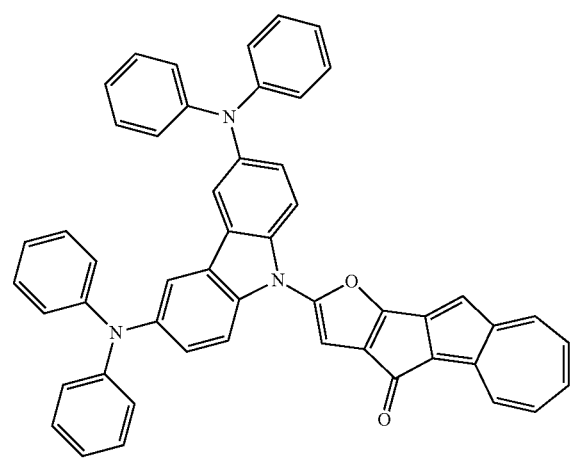
M41
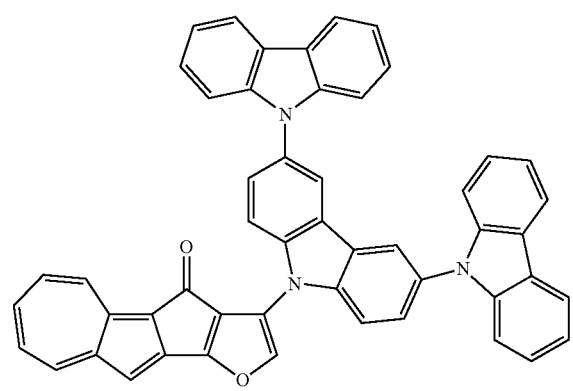
M42
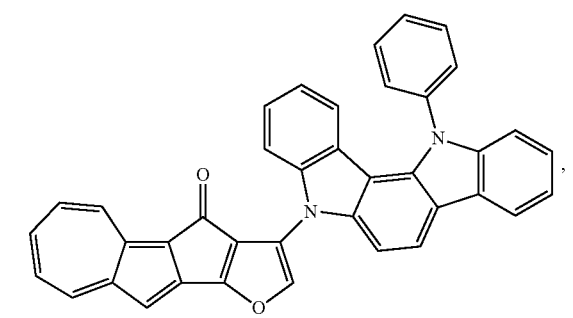
M43
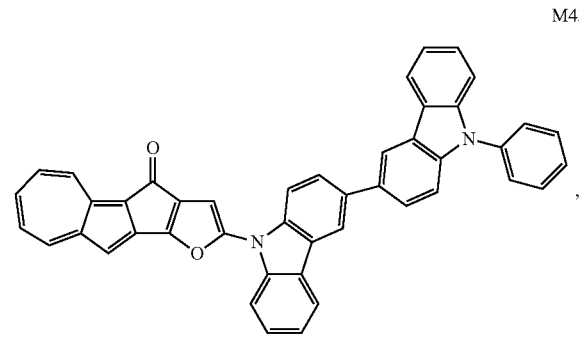
M44
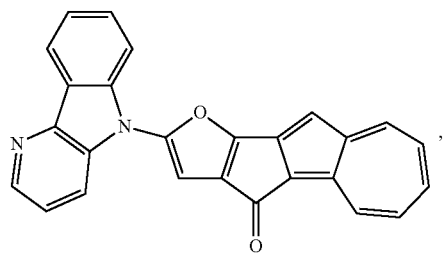
M45
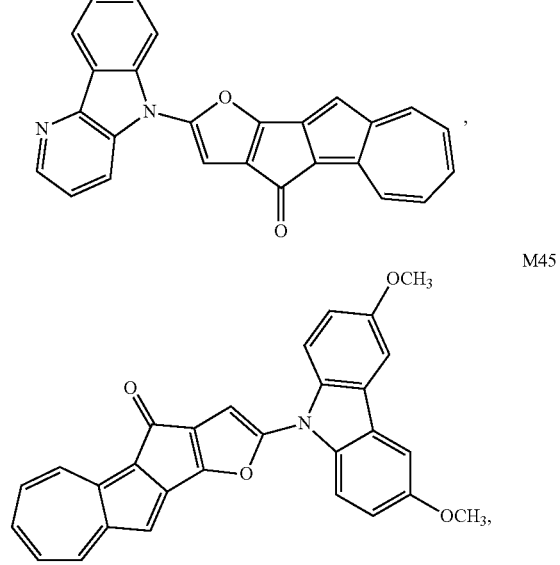
M46
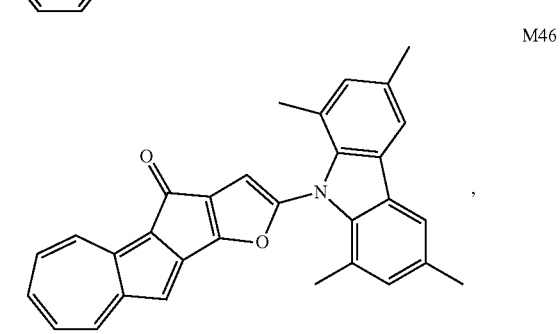
M47
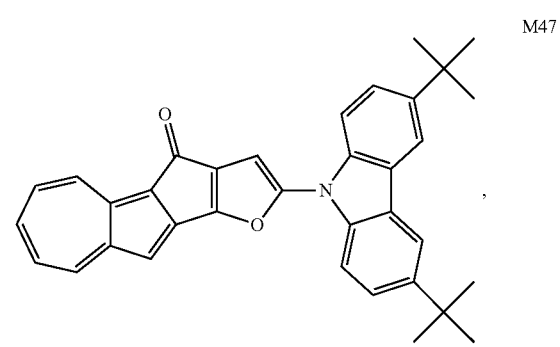
M48
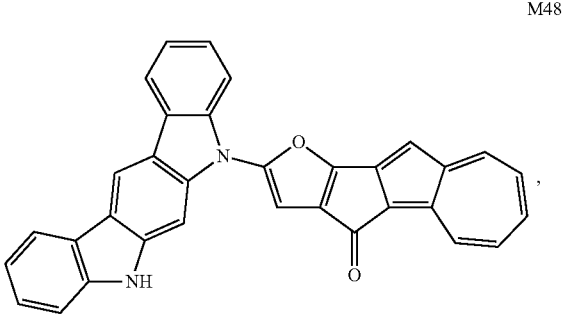

M49
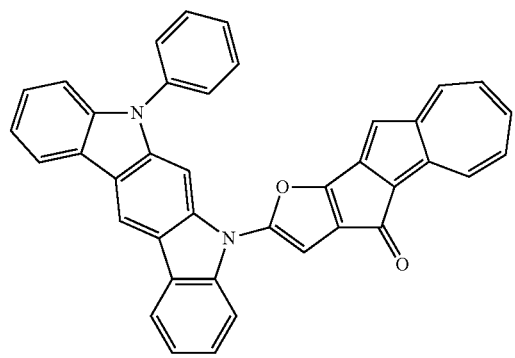
M50
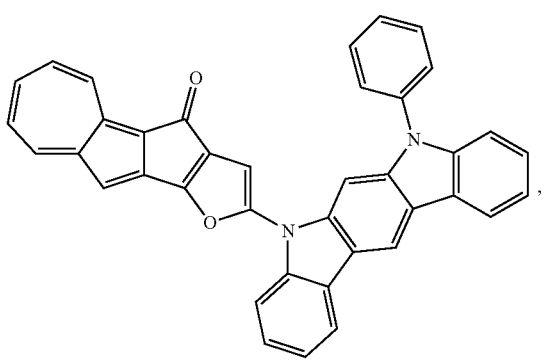
M51
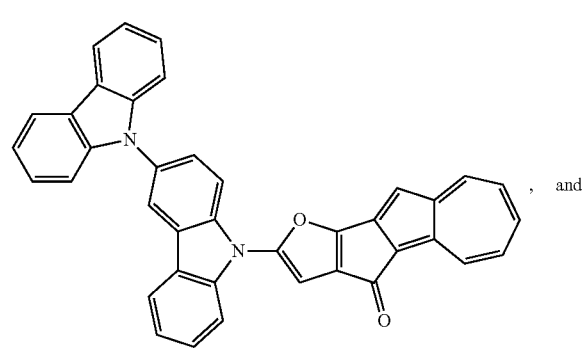
, and
M52
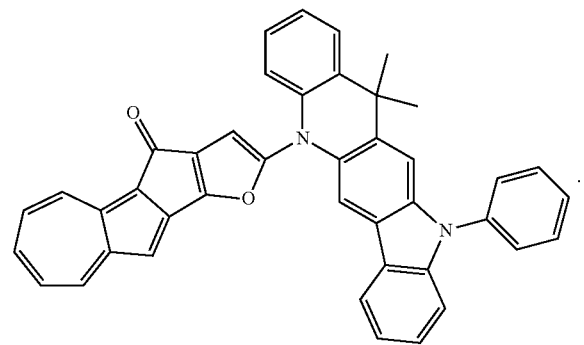
.
In one embodiment of the present disclosure, the azulene ring-containing compound is a compound comprising any one of the following structures:
M53
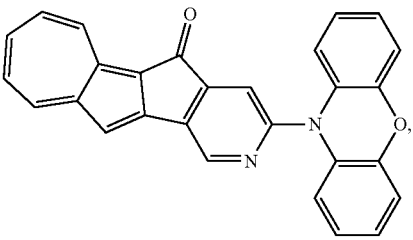
,
M54
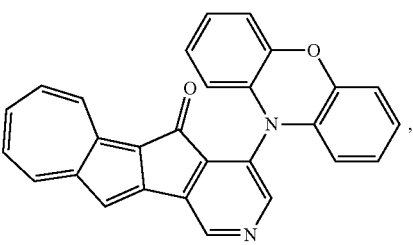
,
M55
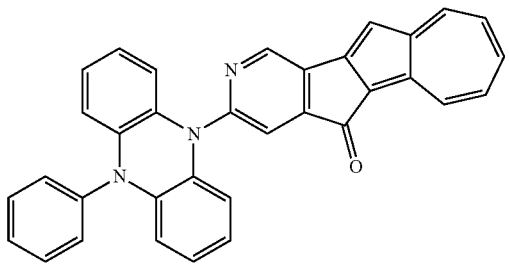
,
M56
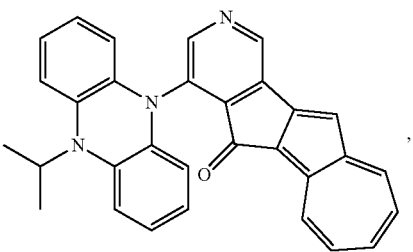
,
M57
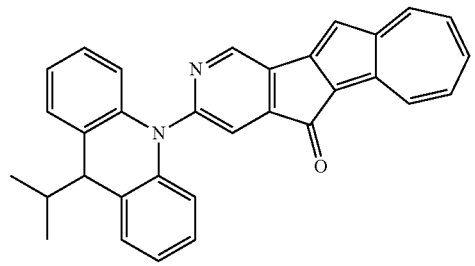
,
M58
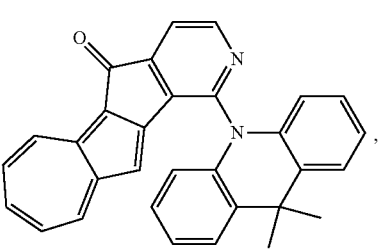
, M59
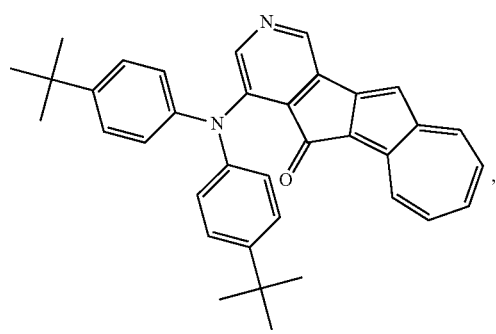
M60
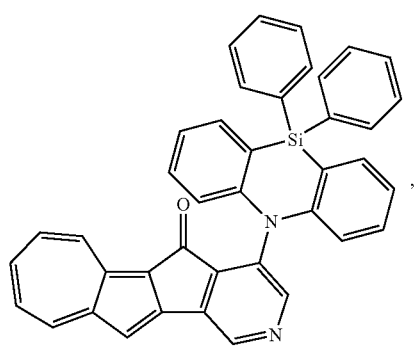
M61
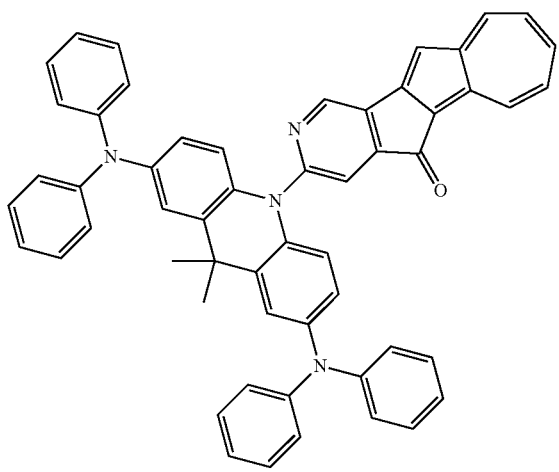
M62
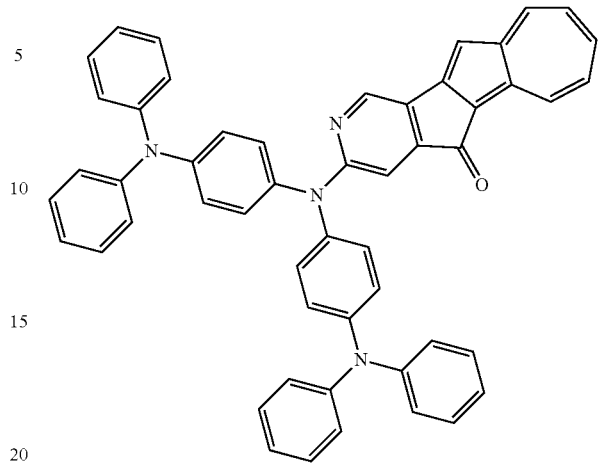
M63
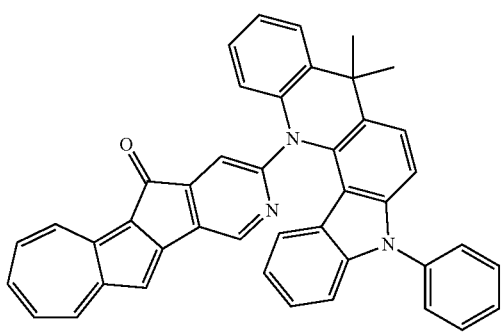
M64
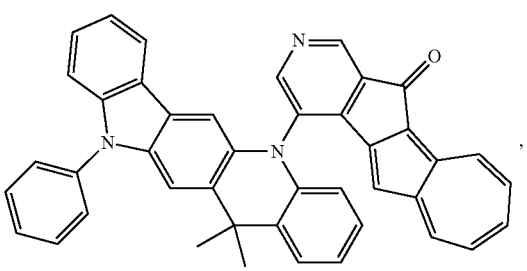
, and
M65
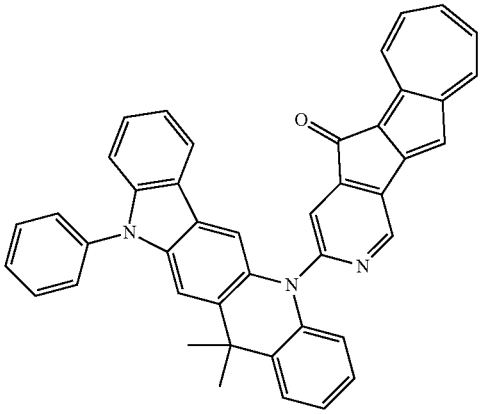
In one embodiment of the present disclosure, the azulene ring-containing compound has an energy level difference between the lowest singlet state energy level $S_1$ and the lowest triplet state energy level $T_1$ below 0.3 eV, ie.

$\Delta E_{st} = E_{S1} - E_{T1} \leq 0.3$ eV; For example, it can be 0.3 eV, 0.28 eV, 0.25 eV, 0.24 eV, 0.23 eV, 0.22 eV, 0.2 eV, 0.18 eV, 0.16 eV, 0.15 eV, 0.13 eV, 0.12 eV, 0.1 eV, 0.08 eV, 0.06 eV, 0.05 eV or 0.03 eV.

In a second aspect, the present disclosure provides a use of the above-mentioned azulene ring-containing compound which is used as a thermally activated delayed fluorescent material.

In a third aspect, the present disclosure provides an organic photoelectric device including an anode, a cathode, and one or more organic thin film layers located between the anode and the cathode; and at least one of the organic thin film layers contains the azulene ring-containing compound provided by the first aspect of the present disclosure.

In one embodiment of the present disclosure, the organic thin film layer includes at least one light-emitting layer; the light-emitting layer includes a host material and a guest material, and the host material or the guest material includes the azulene ring-containing compound provided by the first aspect of the present disclosure.

In one embodiment of the present disclosure, the organic thin film layer further comprises one or a combination of at least two of a hole injection layer, a hole transport layer, an electron blocking layer, a hole blocking layer, an electron transport layer, and an electron injection layer.

In one embodiment of the present disclosure, the organic optoelectronic device comprises an anode, a hole injection layer, a hole transport layer, an electron blocking layer, a light-emitting layer, a hole blocking layer, an electron transport layer, an electron injection layer and a cathode which are sequentially laminated.

The guest material of the light-emitting layer is selected from one or a combination of at least two of the azulene ring-containing compounds provided by the first aspect of the present disclosure.

In an embodiment of the present disclosure, an azulene ring-containing compound comprising the structure of Formula I is prepared by a reaction between an electron donor compound A and an electron acceptor compound, wherein the synthesis route of the electron donor compound A is as follows:

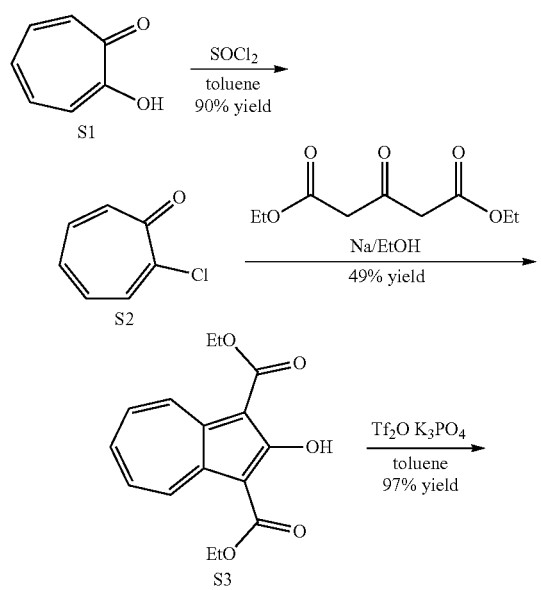

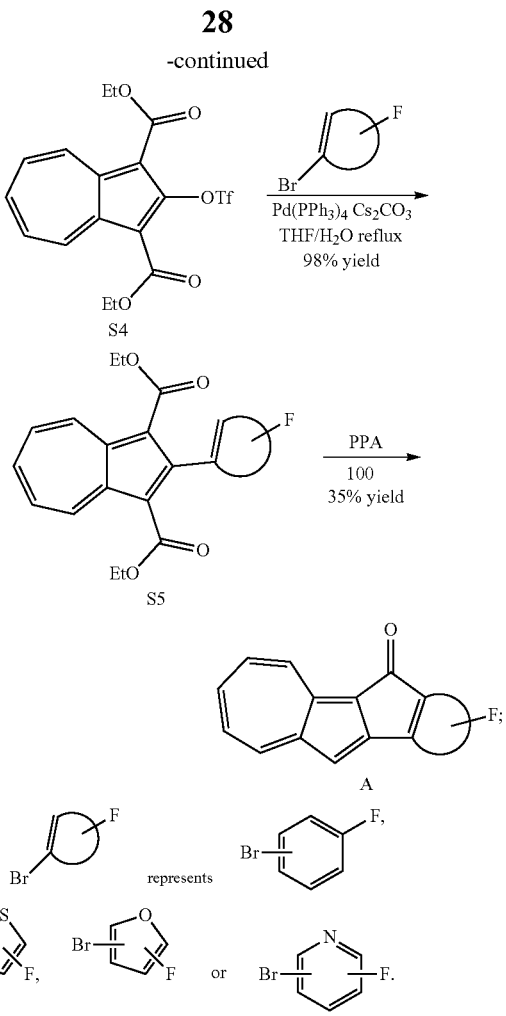

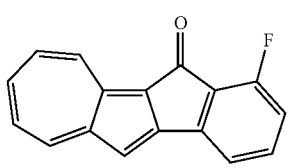

The electron donor compound A1

A1

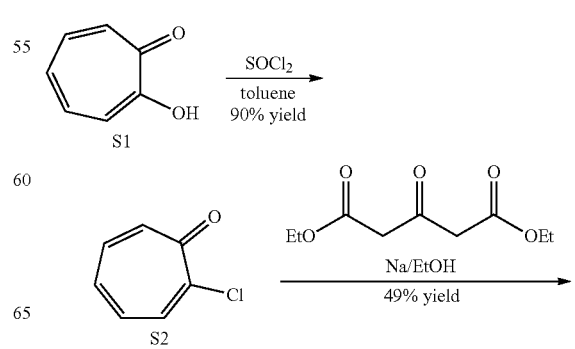

is prepared according to the following synthetic route:

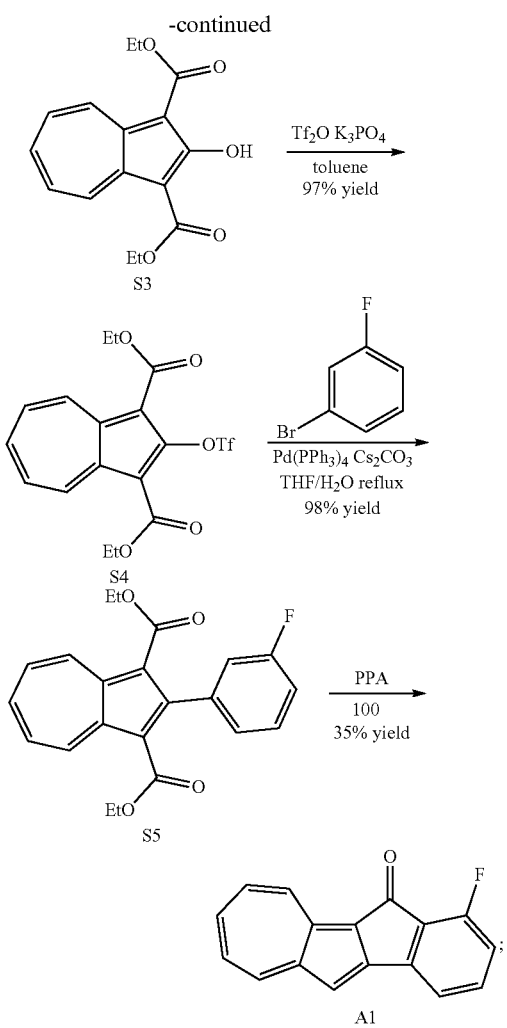

The specific synthesis steps are as follows:

(1) tropolone S1 (10 g, 81.9 mmol) was dissolved in 250 mL of toluene, then thionyl chloride (10.7 g, 90 mmol) was added, a white solid precipitated. The reaction temperature was raised to 120° C. and refluxed for 1.5 h. The white solid disappeared and the solution turned red. Excessive thionyl chloride and toluene were rotary evaporated under reduced pressure to obtain a brown solid, which was separated by column chromatography [V (petroleum ether):V (ethyl acetate)=5:1] to obtain a gray solid, and then petroleum ether was added to reflux, the petroleum ether was rotary evaporated under reduced pressure to obtain 10.5 g of white solid S2 (yield of 93%).

(2) Sodium (4.0 g, 174 mmol) was dissolved in 120 mL of anhydrous ethanol, and then compound diethyl 1,3-acetone dicarboxylate (4.34 g, 21.5 mmol) was added to obtain a milky white solution. A solution of S2 (2.0 g, 14.3 mmol) dissolved in 10 mL of anhydrous ethanol was quickly added to the above system, and the system became a brick red solution. After stirring the reaction at room temperature for 12 h, 200 mL of water was added, then an orange solid precipitated, which was filtered to obtain an orange solid, then it was dissolved in 30 mL of glacial acetic acid, diluted with 100 mL of water, and extracted with dichloromethane for three times, the organic phase was combined and concentrated, then separated through column chromatography [V (petroleum ether):V (ethyl acetate)=5:1] to obtain 2.03 g of orange yellow solid S3 (yield of 49%).

(3) Compound S3 (500 mg, 1.74 mmol) was dissolved in 15 mL of toluene, then 30% K₃PO₄ (3.21 g, 15.1 mmol) in water was added, the mixture was cooled to 0° C. in an ice bath, to which trifluoromethanesulfonic anhydride (671 mg, 2.38 mmol) was slowly added, and the system changed from yellow to blood red. The reaction was performed for 24 h at room temperature, and quenched by adding 100 ml of water, then extracted with dichloromethane for three times. The organic phases were combined, concentrated, and separated by column chromatography [V (petroleum ether):V (dichloromethane)=1:1] to obtain a red solid S4 (1.42 g, yield of 97%).

(4) Compound S4 (500 mg, 1.19 mmol), phenylboronic acid (214 mg, 1.78 mmol), Pd(PPh₃)₄ (138 mg, 0.12 mmol), and CS₂CO₃ (1.16 g, 3.57 mmol) were added to a 100 mL reaction tube in sequence, then replaced with nitrogen for three times, and 20 mL of re-distilled THF and 4 mL of bubbled water were added under the protection of nitrogen. The temperature was then raised to 80° C. and the reaction was stirred for 10 h. After the reaction was completed, the reaction solution was poured into 100 ml of water, extracted with dichloromethane for three times, the organic phases were combined, concentrated, and separated by column chromatography [V (petroleum ether):V (dichloromethane)=4:1] to obtain a purple-red solid S5 (342 mg, yield 98%).

(5) Compound S5 (100 mg, 0.34 mmol) and polyphosphoric acid PPA (40 mmol) were added to a 100 mL reaction flask. Then, the temperature was raised to 100° C. and the reaction was stirred for 6 h. The compound S5 gradually diffused into the whole system, and the color of the system changed from red to gray. After the reaction was completed, the reaction solution was poured into 100 ml of ice water, extracted with ethyl acetate for three times, the organic phases were combined, concentrated, and separated by column chromatography [V (petroleum ether):V (dichloromethane)=2:3] to obtain a gray solid A1 (28 mg, yield 98%).

The electron donor compound A2

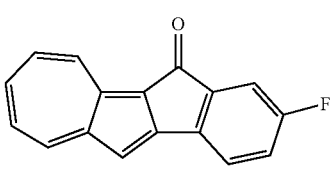

is prepared according to the following synthetic route:

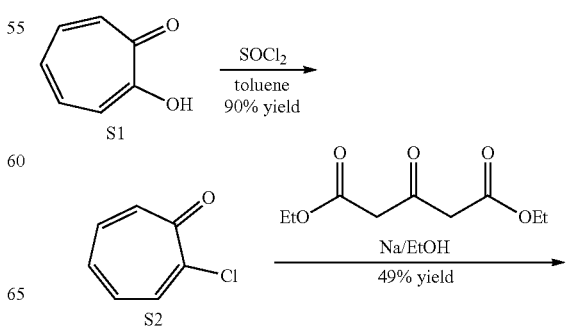

-continued
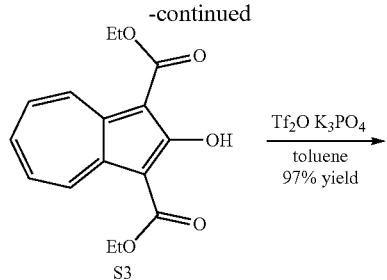
The electron donor compound A3
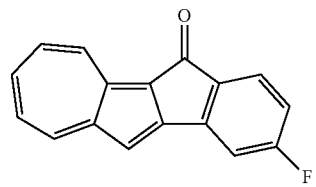
is prepared according to the following synthetic route:
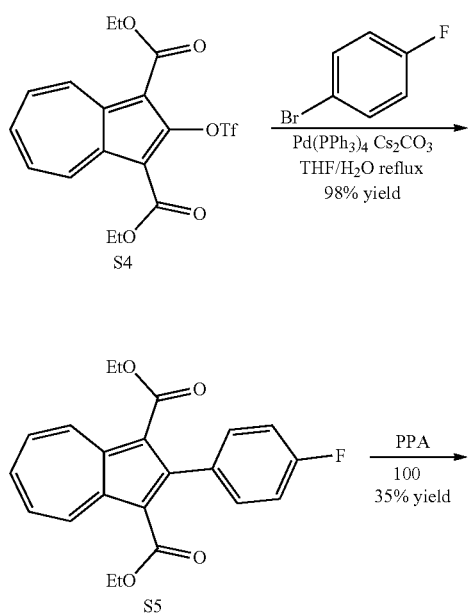
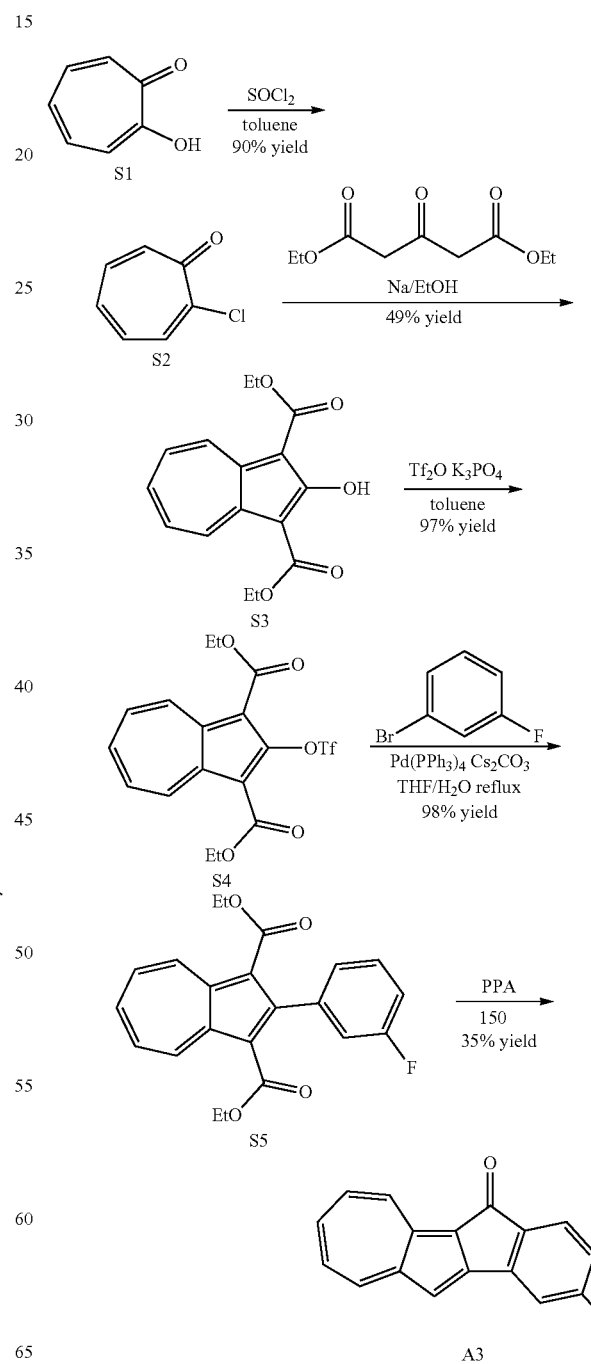
The specific synthesis steps of A2 differ from those of electron donor compound A1 in that
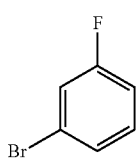
is replaced with
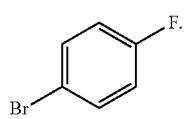

The specific synthesis steps of A3 differ from those of electron donor compound A1 in that the reaction temperature in step (5) is 150° C.

The electron donor compound A4

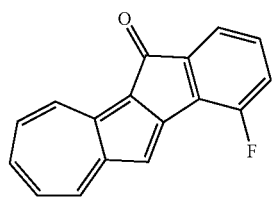

A4 is prepared according to the following synthetic route:

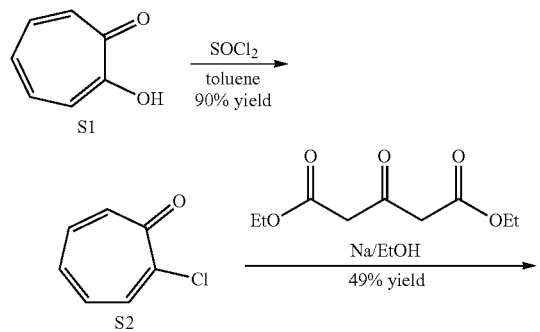

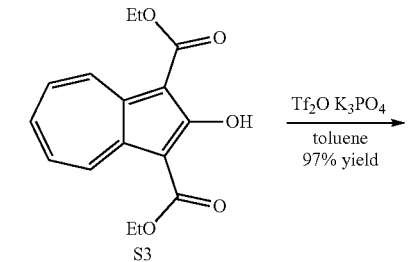

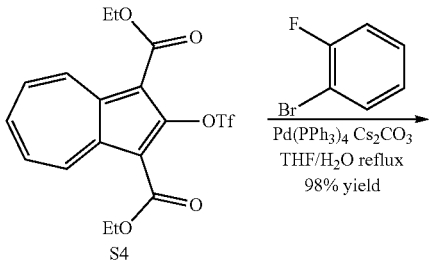

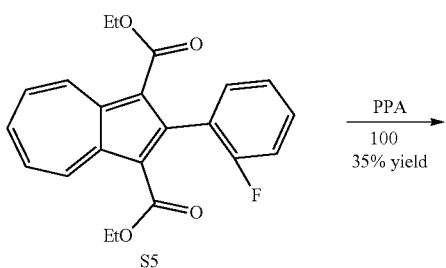

-continued

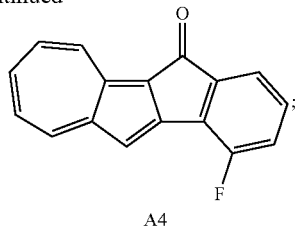

A4

The specific synthesis steps of A4 differ from those of electron donor compound A1 in that

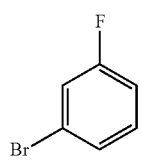

is replaced with

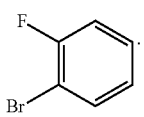

The electron donor compound A5

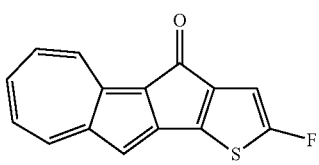

A5 is prepared according to the following synthetic route:

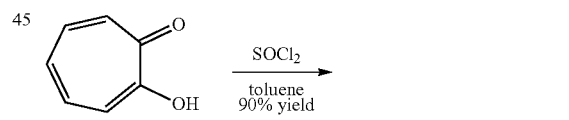

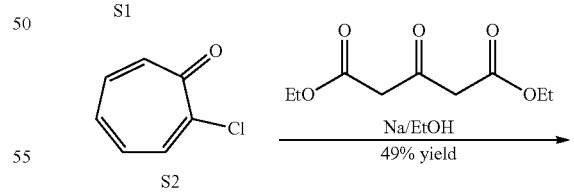

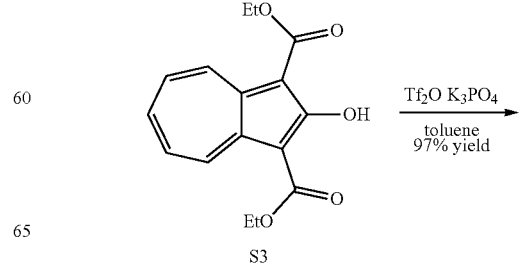

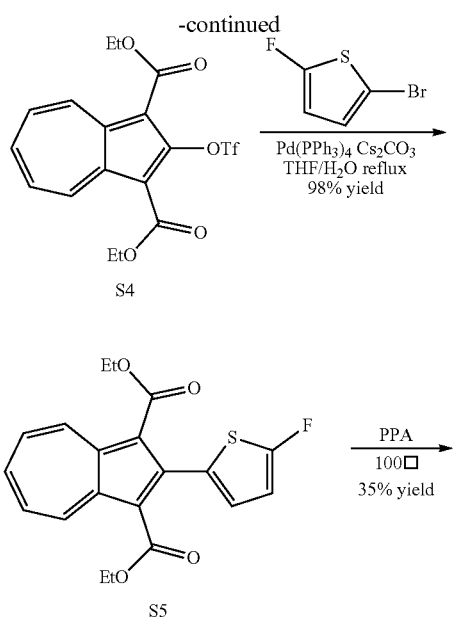
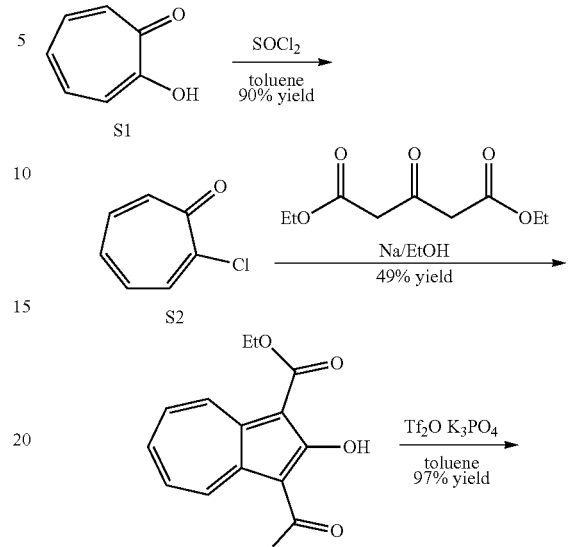
is prepared according to the following synthetic route:
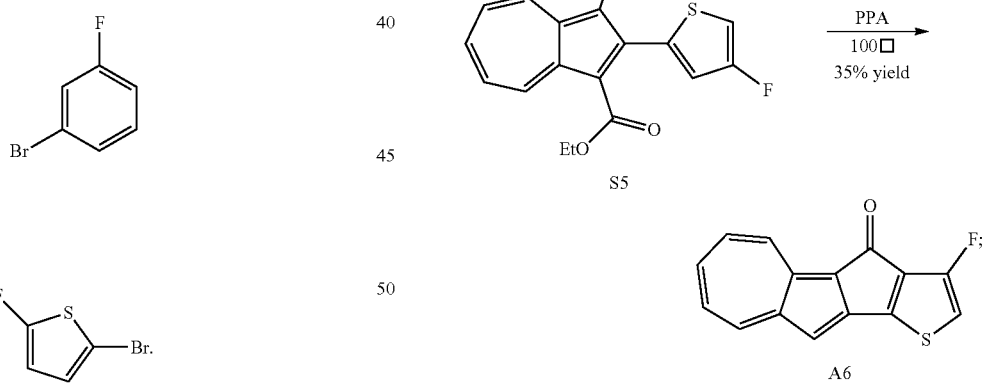
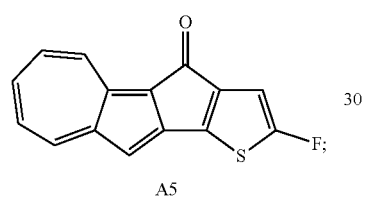
The specific synthesis steps of A5 differ from those of electron donor compound A1 in that
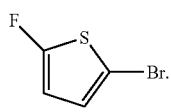
is replaced with
The electron donor compound A6
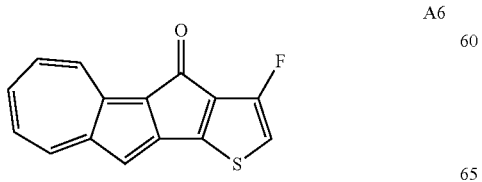
The specific synthesis steps of A6 differ from those of electron donor compound A1 in that
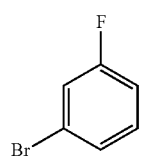

is replaced with

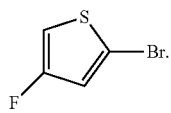

Synthesis steps of electron donor compound A7

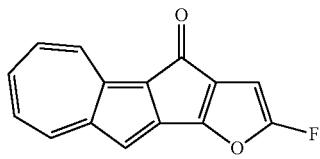

differ from those of electron donor compound A1 in that

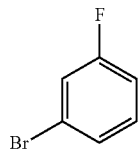

is replaced with

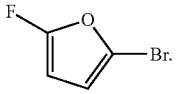

Synthesis steps of electron donor compound A8

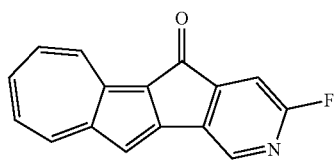

differ from those of electron donor compound A1 in that

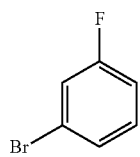

is replaced with

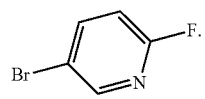

Preparation Example 1

Compound M1 is prepared according to the following synthesis route:

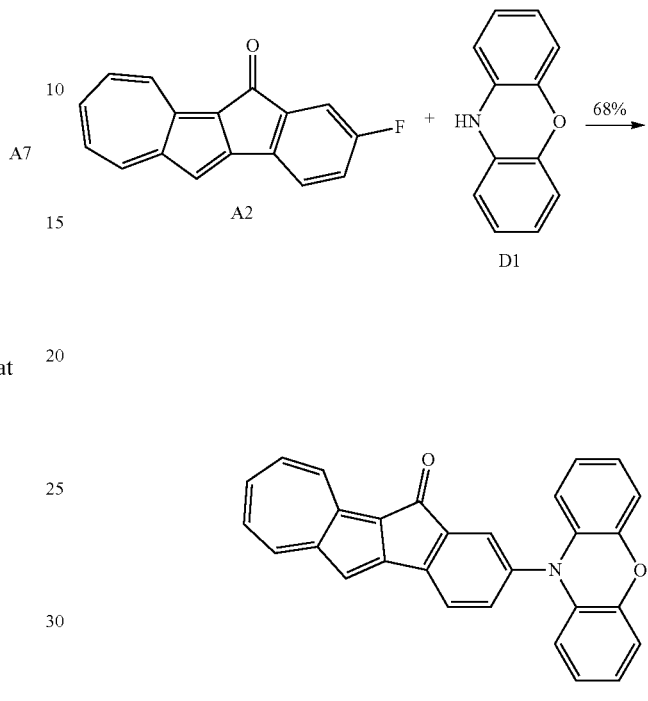

The specific synthesis steps are as follows:

Compound A1 (10 mmol), compound D1 (21.5 mmol), tris (dibenzylideneacetone) dipalladium (0.05 mmol), sodium tert-butoxide (14 mmol), and tert-butylphosphine (0.2 mmol) were placed in a 50 mL of three-necked flask, the reaction system was rapidly degassed and replaced with nitrogen for 3 times while stirring, and 20 mL of toluene was added through a syringe. The mixture was heated under reflux for 3 hours under a stream of nitrogen. After the reaction was completed, the reaction solution was left to cool to room temperature, and then water was added to the reaction solution. The reaction solution was extracted with dichloromethane and washed with saturated brine. After the organic layer was dried over anhydrous sodium sulfate, the solvent was distilled off and refined using column chromatography to obtain the target product M1 (6.8 mmol, yield 68%).

The elemental structure of compound M1 (molecular formula $C_{29}H_{17}NO_2$) was analyzed using an elemental analyzer: Theoretical value (%): C, 84.65; H, 4.16; N, 3.40; O, 7.78. Test value (%): C, 84.61; H, 4.13; N, 3.43; O, 7.83.

ESI-MS (m/z)(M+) was determined by liquid chromatography-mass spectrometry: Theoretical value: 411.13, Test value: 411.15.

Preparation Example 2

Compound M2 is prepared according to the following synthesis route:

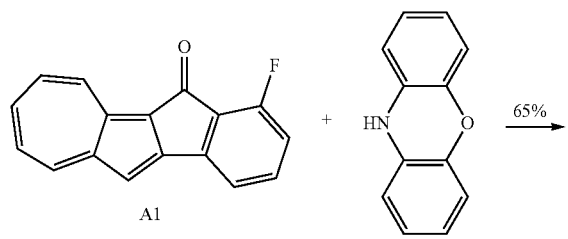

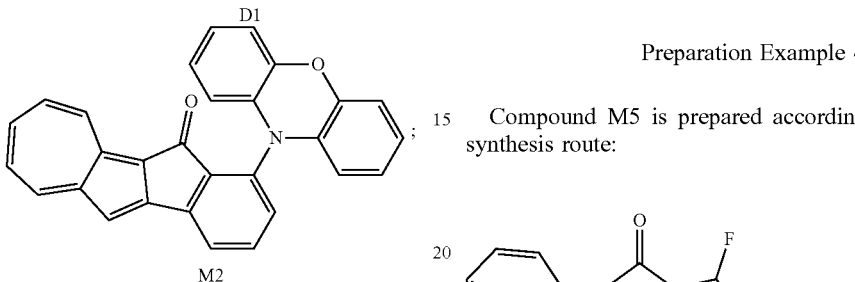

The specific synthesis steps differ from those of Example 1 in that compound A2 is replaced with A1.

The elemental structure of compound M2 (molecular formula $C_{29}H_{17}NO_2$) was analyzed using an elemental analyzer: Theoretical value: C, 84.65; H, 4.16; N, 3.40; O, 7.78. Test value: C, 84.62; H, 4.19; N, 3.41; O, 7.81.

ESI-MS (m/z) (M+) was determined by liquid chromatography-mass spectrometry: Theoretical value: 411.13, Test value: 411.09.

Preparation Example 3

Compound M4 is prepared according to the following synthesis route:

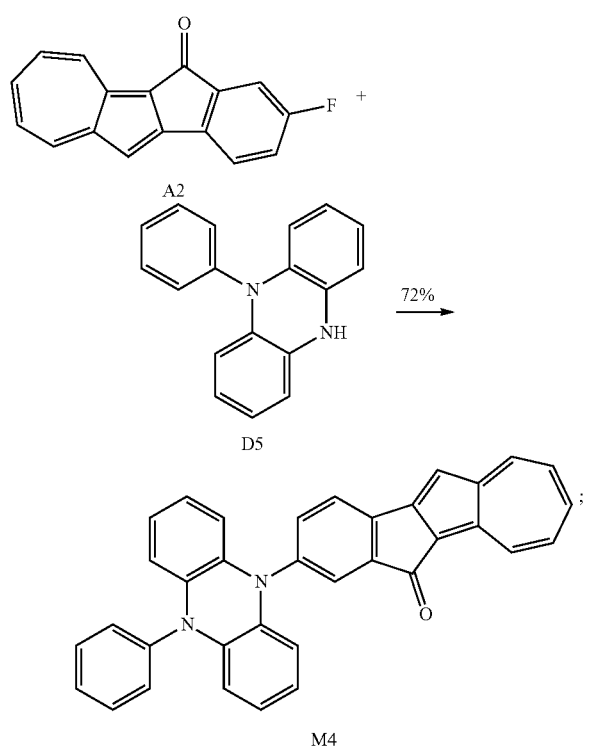

The specific synthesis steps differ from those of Example 1 in that compound D1 is replaced with D5.

The elemental structure of compound M4 (molecular formula $C_{35}H_{22}N_2O$ was analyzed using an elemental analyzer: Theoretical value: C, 86.40; H, 4.56; N, 5.76; O, 3.29. Test value: C, 86.38; H, 4.52; N, 5.79; O, 3.32.

ESI-MS (m/z) (M+) was determined by liquid chromatography-mass spectrometry: Theoretical value: 486.17, Test value: 486.15.

Preparation Example 4

Compound M5 is prepared according to the following synthesis route:

The specific synthesis steps differ from those of Example 1 in that compounds A2 and D1 are replaced with A1 and D2, respectively.

The elemental structure of compound M5 (molecular formula $C_{32}H_{24}N_2O$ was analyzed using an elemental analyzer: Theoretical value: C, 84.93; H, 5.35; N, 6.19; O, 3.54. Test value: C, 84.95; H, 5.38; N, 6.16; O, 3.51.

ESI-MS (m/z) (M+) was determined by liquid chromatography-mass spectrometry: Theoretical value: 452.19, Test value: 452.14.

Preparation Example 5

Compound M7 is prepared according to the following synthesis route:

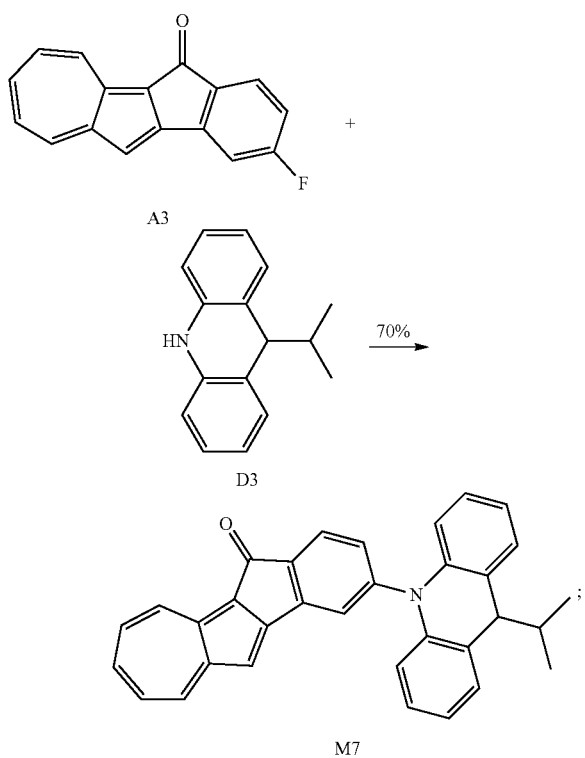

The specific synthesis steps differ from those of Example 1 in that compounds A2 and D1 are replaced with A3 and D3, respectively.

The elemental structure of compound M7 (molecular formula $C_{33}H_{25}NO$) was analyzed using an elemental analyzer: Theoretical value: C, 87.77; H, 5.58; N, 3.10; O, 3.54. Test value: C, 87.77; H, 5.58; N, 3.10; O, 3.54.

ESI-MS (m/z) (M+) was determined by liquid chromatography-mass spectrometry: Theoretical value: 451.19, Test value: 451.11.

Preparation Example 6

Compound M10 is prepared according to the following synthesis route:

The specific synthesis steps differ from those of Example 1 in that compounds A2 and D1 are replaced with A1 and D4, respectively.

The elemental structure of compound M10 (molecular formula $C_{41}H_{27}NOSi$) was analyzed using an elemental analyzer: Theoretical value: C, 85.23; H, 4.71; N, 2.42; O, 2.77; Si, 4.86. Test value: C, 85.13; H, 4.78; N, 2.48; O, 2.82.

ESI-MS (m/z)(M+) was determined by liquid chromatography-mass spectrometry: Theoretical value: 577.19, Test value: 577.15.

Preparation Example 7

Compound M17 is prepared according to the following synthesis route:

The specific synthesis steps differ from those of Example 1 in that compounds A2 and D1 are replaced with A6 and D5, respectively.

The elemental structure of compound M17 (molecular formula $C_{30}H_{22}N_2OS$) was analyzed using an elemental analyzer: Theoretical value: C, 78.57; H, 4.84; N, 6.11; O, 3.49; S, 6.99. Test value: C, 78.61; H, 4.85; N, 6.09; O, 3.48.

ESI-MS (m/z)(M+) was determined by liquid chromatography-mass spectrometry: Theoretical value: 458.15, Test value: 458.18.

Preparation Example 8

Compound M20 is prepared according to the following synthesis route:

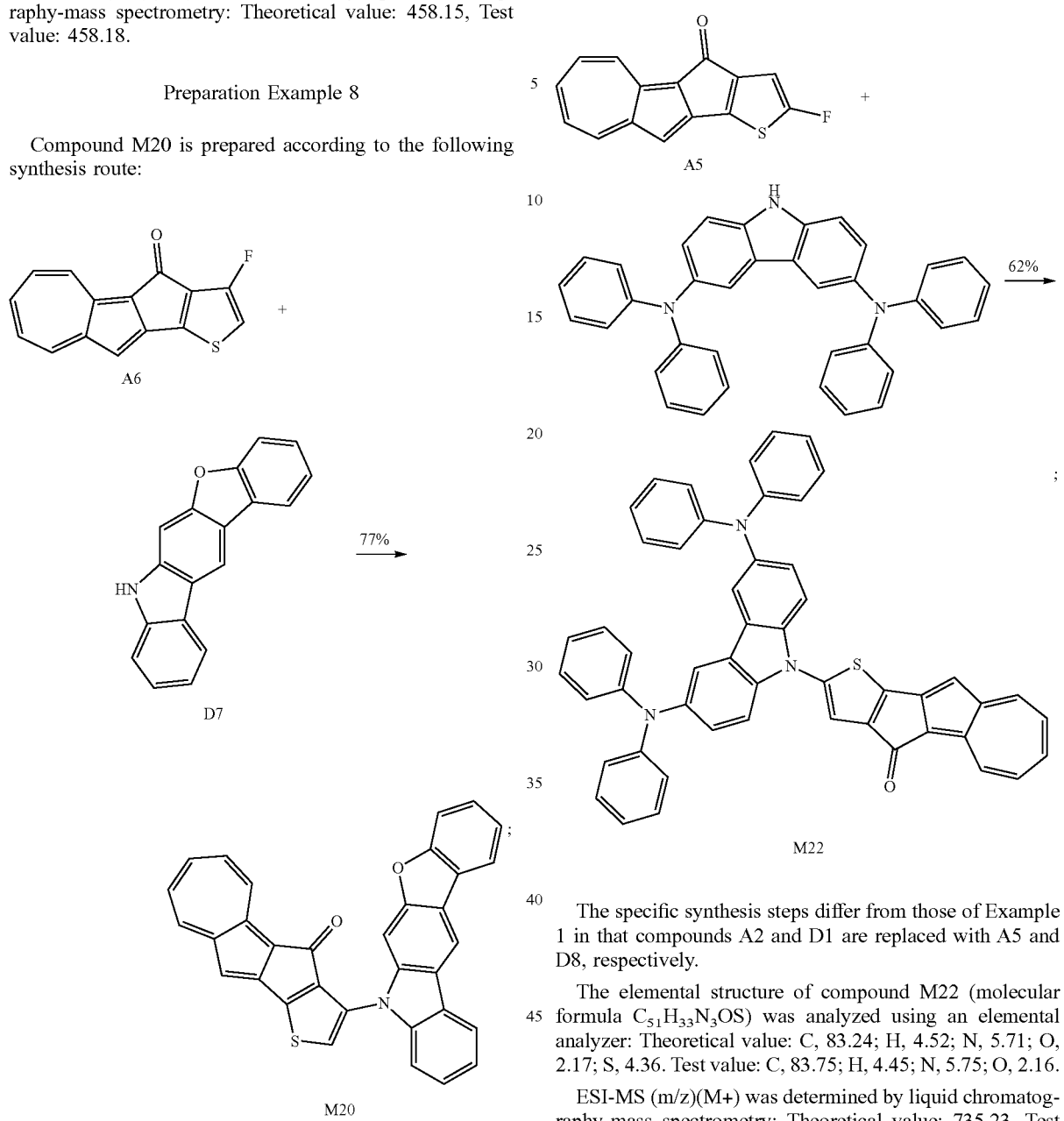

The specific synthesis steps differ from those of Example 1 in that compounds A2 and D1 are replaced with A6 and D7, respectively.

The elemental structure of compound M20 (molecular formula $C_{33}H_{17}NO_2S$) was analyzed using an elemental analyzer: Theoretical value: C, 80.63; H, 3.49; N, 2.85; O, 6.51; S, 6.52. Test value: C, 80.41; H, 3.45; N, 2.94; O, 6.59.

ESI-MS (m/z)(M+) was determined by liquid chromatography-mass spectrometry: Theoretical value: 491.10, Test value: 491.25.

Preparation Example 9

Compound M22 is prepared according to the following synthesis route:

The specific synthesis steps differ from those of Example 1 in that compounds A2 and D1 are replaced with A5 and D8, respectively.

The elemental structure of compound M22 (molecular formula $C_{51}H_{33}N_3OS$) was analyzed using an elemental analyzer: Theoretical value: C, 83.24; H, 4.52; N, 5.71; O, 2.17; S, 4.36. Test value: C, 83.75; H, 4.45; N, 5.75; O, 2.16.

ESI-MS (m/z)(M+) was determined by liquid chromatography-mass spectrometry: Theoretical value: 735.23, Test value: 735.65.

Preparation Example 10

Compound M24 is prepared according to the following synthesis route:

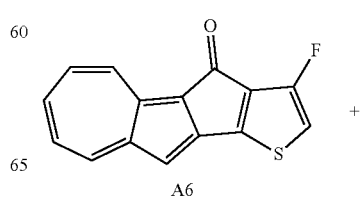

-continued

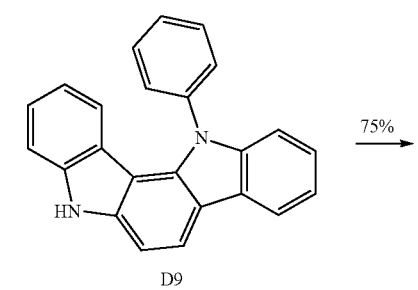

D9

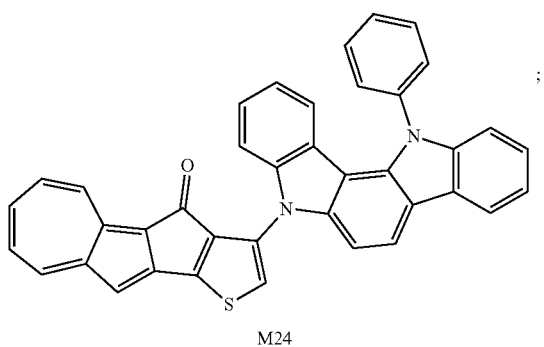

M24

The specific synthesis steps differ from those of Example 1 in that compounds A2 and D1 are replaced with A6 and D9, respectively.

The elemental structure of compound M24 (molecular formula $C_{39}H_{22}N_2OS$) was analyzed using an elemental analyzer: Theoretical value: C, 82.66; H, 3.91; N, 4.94; O, 2.82; S, 5.66. Test value: C, 82.25; H, 3.89; N, 4.95; O, 2.84.

ESI-MS (m/z)(M+) was determined by liquid chromatography-mass spectrometry: Theoretical value: 566.15, Test value: 566.42.

Preparation Example 11

Compound M27 is prepared according to the following synthesis route:

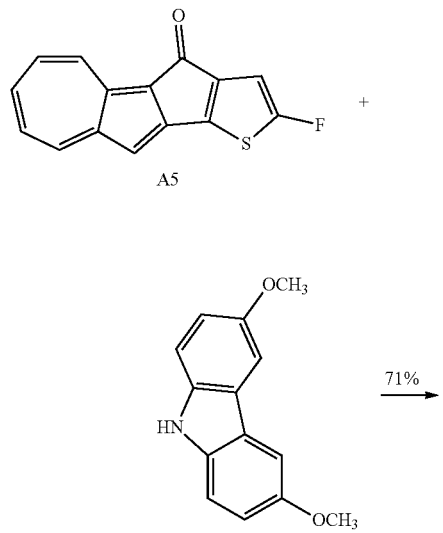

-continued

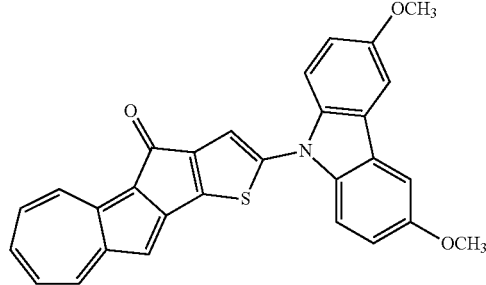

M27

The specific synthesis steps differ from those of Example 1 in that compounds A2 and D1 are replaced with A5 and D6, respectively.

The elemental structure of compound M27 (molecular formula $C_{29}H_{19}NO_3S$) was analyzed using an elemental analyzer: Theoretical value: C, 75.47; H, 4.15; N, 3.03; O, 10.40; S, 6.95. Test value: C, 75.14; H, 4.19; N, 3.10; O, 10.19.

ESI-MS (m/z)(M+) was determined by liquid chromatography-mass spectrometry: Theoretical value: 461.11, Test value: 461.58.

Preparation Example 12

Compound M35 is prepared according to the following synthesis route:

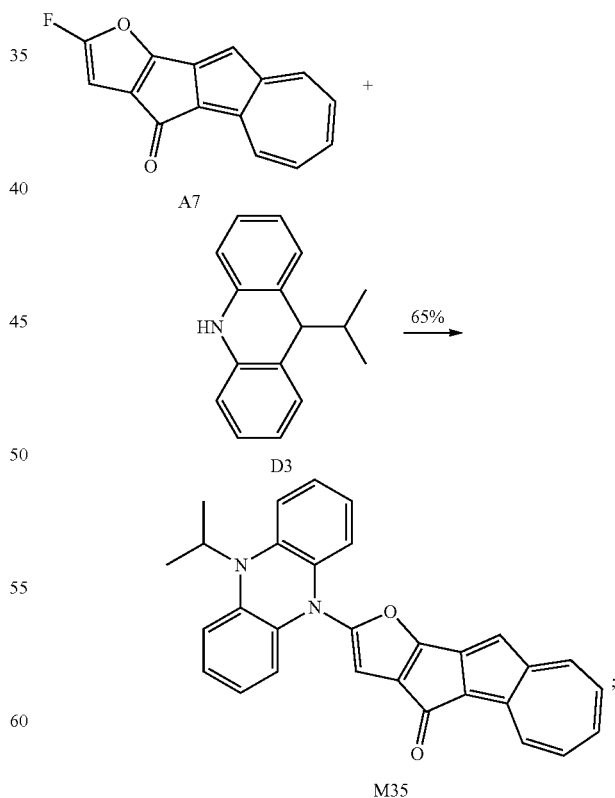

M35

The specific synthesis steps differ from those of Example 1 in that compounds A2 and D1 are replaced with A7 and D3, respectively.

The elemental structure of compound M35 (molecular formula $C_{30}H_{22}N_2O_2$) was analyzed using an elemental analyzer: Theoretical value: C, 81.43; H, 5.01; N, 6.33; O, 7.23. Test value: C, 81.31; H, 5.09; N, 6.38; O, 7.28.

ESI-MS (m/z)(M+) was determined by liquid chromatography-mass spectrometry: Theoretical value: 442.17, Test value: 442.54.

Preparation Example 13

Compound M57 is prepared according to the following synthesis route:

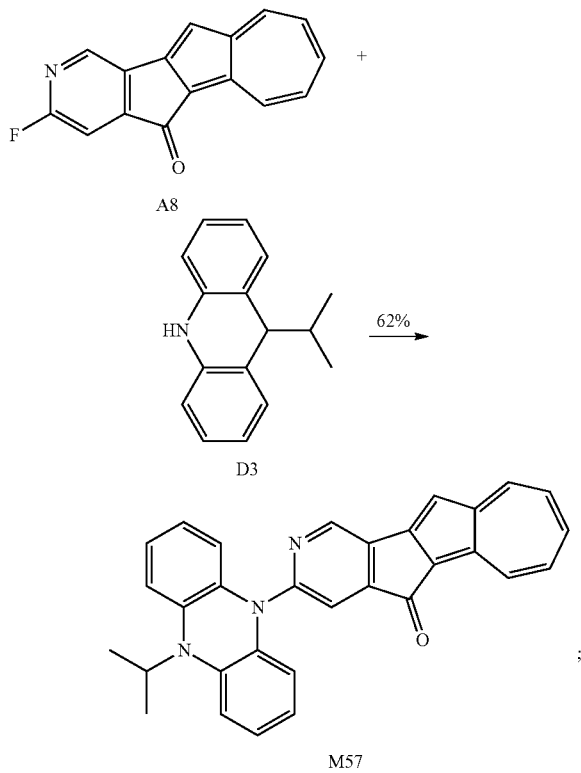

The specific synthesis steps differ from those of Example 1 in that compounds A2 and D1 are replaced with A8 and D3, respectively.

The elemental structure of compound M57 (molecular formula $C_{31}H_{22}N_2O$) was analyzed using an elemental analyzer: Theoretical value: C, 84.91; H, 5.06; N, 6.39; O, 3.65. Test value: C, 84.72; H, 5.11; N, 6.46; O, 3.72.

ESI-MS (m/z)(M+) was determined by liquid chromatography-mass spectrometry: Theoretical value: 438.17, Test value: 438.45.

The HOMO (highest occupied molecular orbital) energy level, the LUMO (lowest unoccupied molecular orbital) energy level, the lowest singlet energy level $E_{S1}$ and the lowest triplet energy level $E_{T1}$ of the azulene ring-containing compound having the structure of Formula I provided by the preparation example of the present disclosure were simulated and calculated using Gaussian 09 software, and the results are shown in Table 1 below:

TABLE 1

| Compounds | HOMO energy level (eV) | LUMO energy level (eV) | $E_{S1}$ (eV) | $E_{T1}$ (eV) | $\Delta E_{st}$ (eV) | $E_g$ (eV) |
|---|---|---|---|---|---|---|
| M1 | −4.88 | −2.86 | 2.12 | 1.89 | 0.23 | 2.02 |
| M2 | −4.70 | −2.78 | 2.00 | 1.85 | 0.15 | 1.98 |
| M4 | −4.24 | −2.77 | 1.604 | 1.597 | 0.037 | 1.47 |
| M5 | −5.02 | −2.78 | 2.12 | 1.87 | 0.25 | 2.24 |
| M17 | −4.42 | −2.84 | 1.72 | 1.65 | 0.07 | 1.58 |
| M20 | −4.80 | −2.82 | 1.85 | 1.72 | 0.13 | 1.98 |
| M22 | −4.92 | −2.79 | 1.84 | 1.69 | 0.15 | 2.13 |
| M24 | −4.99 | −2.81 | 1.95 | 1.84 | 0.11 | 2.18 |
| M35 | −4.83 | −2.79 | 1.80 | 1.71 | 0.09 | 2.04 |
| M57 | −4.90 | −2.81 | 1.81 | 1.70 | 0.11 | 2.09 |

In Table 1, $\Delta E_{st}=E_{S1}-E_{T1}$, and $E_g$ is the HOMO-LUMO energy level difference.

It can be seen from Table 1 that the $\Delta E_{ST}$ of all the compounds is less than 0.3 eV, and there is a small energy level difference between the singlet and triplet states, which is conducive to reverse intersystem crossing and has a delayed fluorescence effect.

Hereinafter, the present disclosure will be explained in detail through the following examples in order to better understand the aspects and advantages of the present disclosure. It should be understood, however, that the following examples are non-limiting and are intended only to illustrate certain embodiments of the disclosure.

Example 1

An organic light-emitting device was provided in this embodiment. As shown in FIG. 1, the organic light-emitting device includes a glass substrate 1, an ITO anode 2, a first hole transport layer 3, a second hole transport layer 4, a light-emitting layer 5, a first electron transport layer 6, and a second electron transport layer 7, a cathode 8 (magnesium-silver electrode with a magnesium-silver mass ratio of 9:1) and a cap layer 9 (CPL), wherein the ITO anode 2 has a thickness of 15 nm, and the first hole transport layer 3 has a thickness of 10 nm, the second hole transport layer 4 has a thickness of 95 nm, the light-emitting layer 5 has a thickness of 30 nm, the first electron transport layer 6 has a thickness of 35 nm, the second electron transport layer 7 has a thickness of 5 nm, the cathode 8 has a thickness of 15 nm and the cathode cover layer 9 (cap layer or CPL) has a thickness of 100 nm.

The preparation steps of the organic light-emitting device in this example are as follows:

1) cutting the composite material of ITO anode 2 and the glass substrate 1 into a size of 50 mm×50 mm×0.7 mm, sonicating in isopropanol and deionized water for 30 minutes, respectively, and then exposing to ozone for about 10 minutes for cleaning; mounting the obtained glass substrate with ITO anode to a vacuum deposition apparatus;

2) on the ITO anode layer 2, evaporating the first hole transport layer material HAT-CN by vacuum evaporation to a thickness of 10 nm, and this layer was used as the first hole transport layer 3;

3) vacuum-evaporating second hole transport layer material TAPC on the first hole transport layer 3 to a thickness of 95 nm as the second hole transport layer 4;

4) co-depositing a light-emitting layer 5 on the hole transport layer 4, wherein compound M1 was used as a guest material, DBP was used as a host material, and a mass ratio of DBP to compound M1 was 19:1, and the thickness was 30 nm;

5) vacuum-evaporating the first electron transport layer 6 on the light-emitting layer 5, the material of the first electron transport layer 6 was BPhen and the thickness was 35 nm;

6) vacuum-evaporating the second electron transport layer 7 on the first electron transport layer 6, the material of the second electron transport layer 7 was Alq3, and the thickness was 5 nm;

7) vacuum-evaporating a magnesium-silver electrode on the second electron transport layer 7, wherein a mass ratio of Mg to Ag was 9:1, and the thickness was 15 nm, as the cathode 8; and 8) vacuum-evaporating a hole-type material CBP with a high refractive index to a thickness of 100 nm on the cathode 8, which was used as a cathode cover layer 9 (cap layer or CPL).

Among them, structural formulas corresponding to the abbreviations of the materials used were as follows:

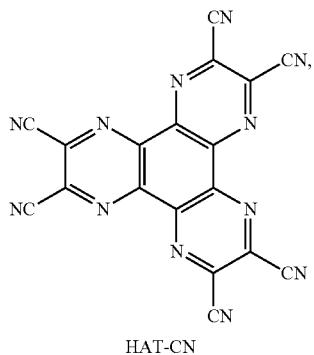

HAT-CN

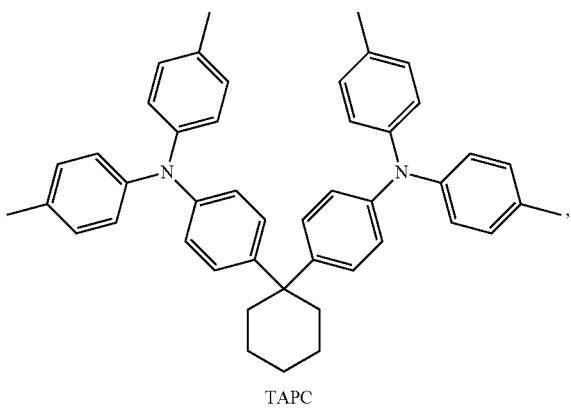

TAPC

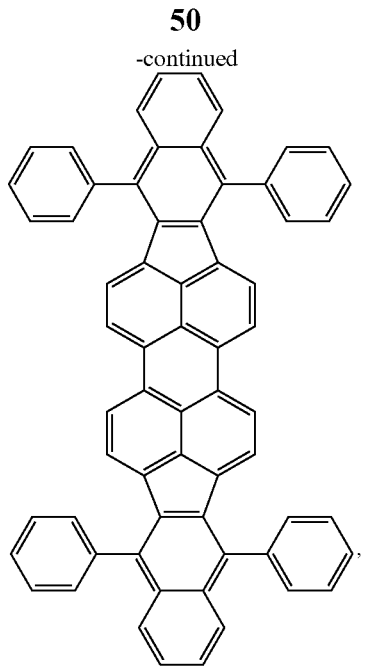

DBP

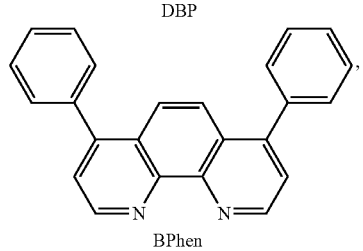

BPhen

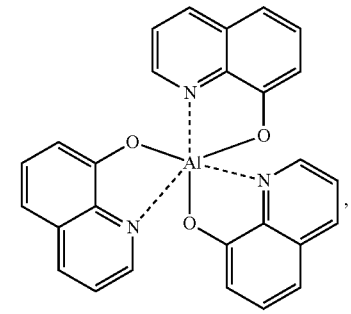

Alq$_3$

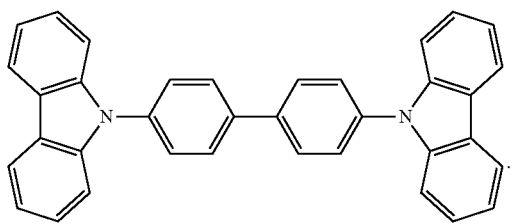

CBP

Example 2

An organic light-emitting device was provided, which is different from Example 1 in that compound M1 is replaced with compound M2.

Example 3

An organic light-emitting device was provided, which is different from Example 1 in that compound M1 is replaced with compound M4.

Example 4

An organic light-emitting device was provided, which is different from Example 1 in that compound M1 is replaced with compound M5.

Example 5

An organic light-emitting device was provided, which is different from Example 1 in that compound M1 is replaced with compound M17.

Example 6

An organic light-emitting device was provided, which is different from Example 1 in that compound M1 is replaced with compound M20.

Example 7

An organic light-emitting device was provided, which is different from Example 1 in that compound M1 is replaced with compound M22.

Example 8

An organic light-emitting device was provided, which is different from Example 1 in that compound M1 is replaced with compound M24.

Example 9

An organic light-emitting device was provided, which is different from Example 1 in that compound M1 is replaced with compound M35.

Example 10

An organic light-emitting device was provided, which is different from Example 1 in that compound M1 is replaced with compound M57.

Comparative Example 1

An organic light-emitting device was provided, which is different from Example 1 in that compound M1 is replaced with compound DBP.

Performance Evaluation of Organic Photoelectric Device:

A Keithley 2365A digital nanovoltmeter was used to test currents of organic photoelectric devices provided in Examples 1-12 and Comparative Example 1 at different voltages, and then the current was divided by a light-emitting area to obtain a current density of the organic photoelectric device at different voltages. A Konicaminolta CS-2000 spectroradiometer was used to test luminance and radiant energy flux density of the organic optoelectronic device manufactured according to test examples and comparative examples under different voltages. According to the current density and luminance of the organic optoelectronic device under different voltages, the current efficiency (CE, in Cd/A) and external quantum efficiency EQE at the same current density (10 mA/cm$^2$) were obtained. The results are shown in Table 2 below:

TABLE 2

| Test items | Guest material of light-emitting layer | Driving voltage [V] | CE(Cd/A) | EQE(%) | light-emitting color |
|---|---|---|---|---|---|
| Example 1 | M1 | 4.21 | 13.14 | 7.3 | Red |
| Example 2 | M2 | 3 | 13.87 | 7.9 | Red |
| Example 3 | M4 | 3.82 | 15.80 | 9.3 | Red |
| Example 4 | M5 | 4.05 | 13.86 | 8.4 | Red |
| Example 5 | M17 | 3.90 | 14.01 | 8.9 | Red |
| Example 6 | M20 | 4.13 | 14.23 | 9.0 | Red |
| Example 7 | M22 | 4.19 | 13.92 | 8.2 | Red |
| Example 8 | M24 | 4.08 | 14.59 | 8.4 | Red |
| Example 9 | M35 | 4.01 | 14.92 | 9.1 | Red |
| Example 10 | M57 | 4.16 | 14.43 | 8.2 | Red |
| Comparative Example 1 | DBP | 4.32 | 9.81 | 5.8 | Red |

As can be seen from the results in Table 2, compared with Comparative Example 1, the organic light-emitting device using the azulene ring-containing compound provided by the present disclosure as a light-emitting layer guest material has lower driving voltage, higher current efficiency, and higher external quantum efficiency. Its driving voltage at a current density of 10 mA/cm$^2$ is ≤4.3 V, its current efficiency is ≥13 Cd/A, and its external quantum efficiency is ≥7%. It is shown that the azulene ring-containing compound provided by the present disclosure can be used in an organic light-emitting device as a thermally activated delayed fluorescent material, which can effectively improve device efficiency and reduce device power consumption.

Applicant has stated that the embodiments described above are merely specific embodiments of the present disclosure, however the protection scope of the present disclosure is not limited thereto, and those skilled in the art should know, any variations or substitutions easily occurred to those skilled in the art within the technical scope disclosed by the present disclosure, are all fall within the scopes of protection and disclosure of the present disclosure.

What is claimed is:

1. An azulene ring-containing compound, wherein the azulene ring-containing compound is a compound represented by the structure of Formula I:

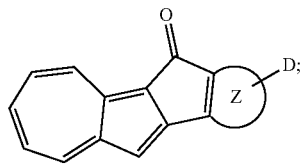

Formula I in Formula I, Z ring

is an unsaturated five-membered ring or an unsaturated six-membered ring, and D is an electron-donating group.

2. The azulene ring-containing compound according to claim 1, wherein the Z ring in Formula I is a benzene ring, a thiophene ring, a furan ring, or a pyridine ring.

3. The azulene ring-containing compound according to claim 1, wherein the azulene ring-containing compound is a compound represented by the structure of Formula II:

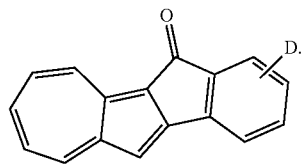

Formula II

4. The azulene ring-containing compound according to claim 1, wherein the azulene ring-containing compound is a compound represented by the structure of Formula III:

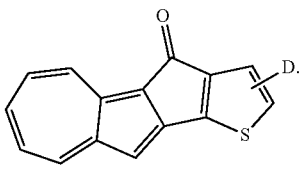

Formula III

5. The azulene ring-containing compound according to claim 1, wherein the azulene ring-containing compound is a compound represented by the structure of Formula IV:

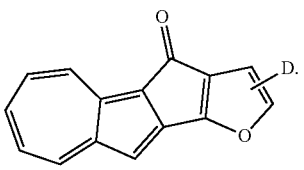

Formula IV

6. The azulene ring-containing compound according to claim 1, wherein the azulene ring-containing compound is a compound represented by the structure of Formula V:

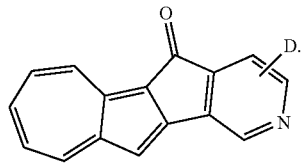

Formula V

7. The azulene ring-containing compound according to claim 1, wherein D is an electron-donating group containing nitrogen.

8. The azulene ring-containing compound according to claim 7, wherein D is selected from any one of the following groups:

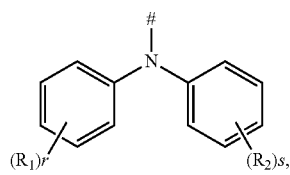

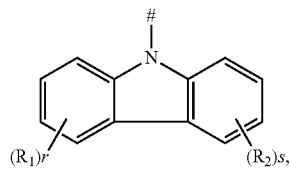

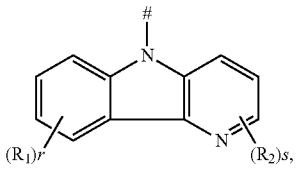

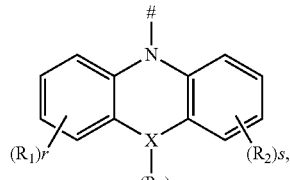

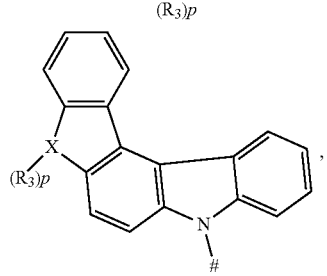

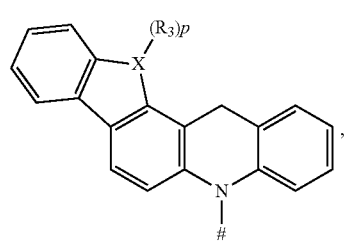

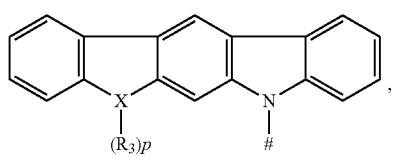

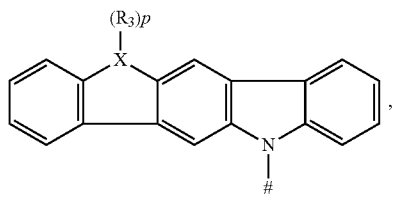

-continued

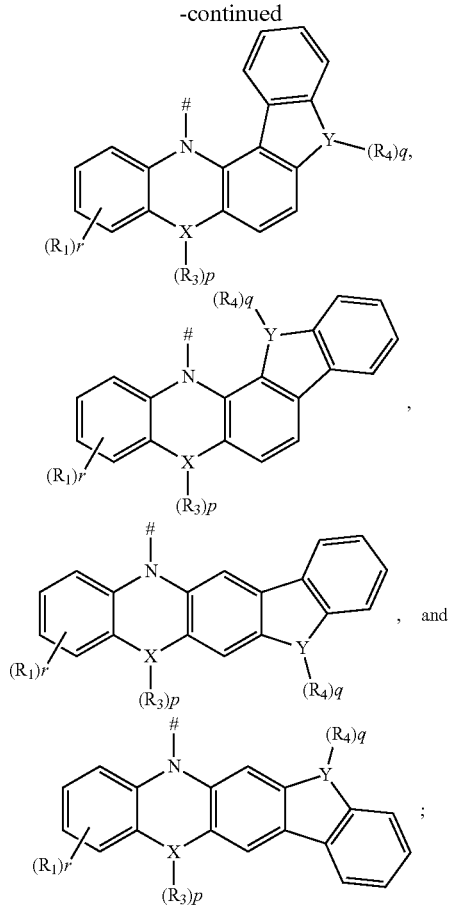

wherein, X and Y each is independently selected from one of a carbon atom, a nitrogen atom, an oxygen atom, a sulfur atom, and a silicon atom;

$R_1$ and $R_2$ each is independently selected from any one of a substituted or unsubstituted alkyl group having 1 to 20 carbon atoms, a substituted or unsubstituted alkoxy group having 1 to 20 carbon atoms, a substituted or unsubstituted phenyl group, a substituted or unsubstituted carbazolyl, a substituted or unsubstituted diphenylamino, r and s each is independently 0, 1, 2 or 3;

$R_3$ and $R_4$ each is independently selected from any one of a hydrogen atom, a substituted or unsubstituted alkyl group having 1 to 20 carbon atoms, a substituted or unsubstituted alkoxy group having 1 to 20 carbon atoms, a substituted or unsubstituted phenyl group, a substituted or unsubstituted carbazolyl, a substituted or unsubstituted diphenylamino, p and q each is independently 0, 1, or 2;

represents a linking site of a group.

9. The azulene ring-containing compound according to claim 8, wherein the substituted or unsubstituted phenyl group has a structural formula of

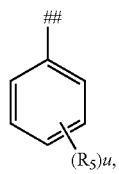

the substituted or unsubstituted carbazolyl group has a structural formula of

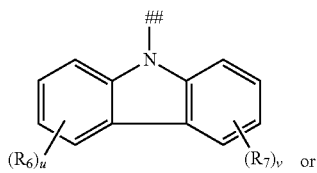

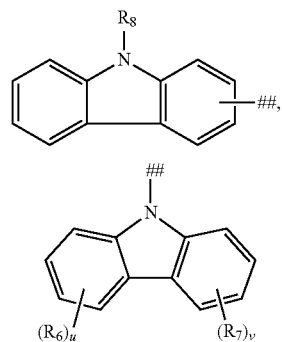

and the substituted or unsubstituted diphenylamino group has a structural formula of

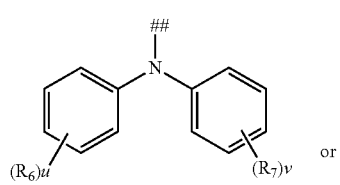

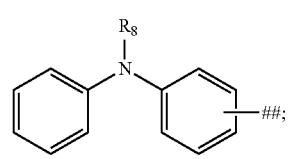

wherein, $R_5$, $R_6$, $R_7$ and $R_8$ each is independently selected from any one of an alkyl group having 1 to 20 carbon atoms, an alkoxy group having 1 to 20 carbon atoms, and a phenyl group;

u and v each is independently 0, 1, 2 or 3;

represents a linking site of a group.

10. The azulene ring-containing compound according to claim 1, wherein D is selected from any one of the following groups:

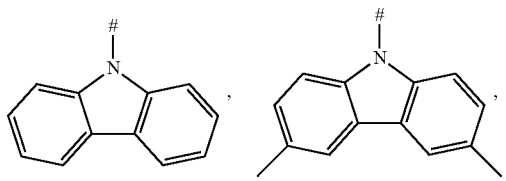

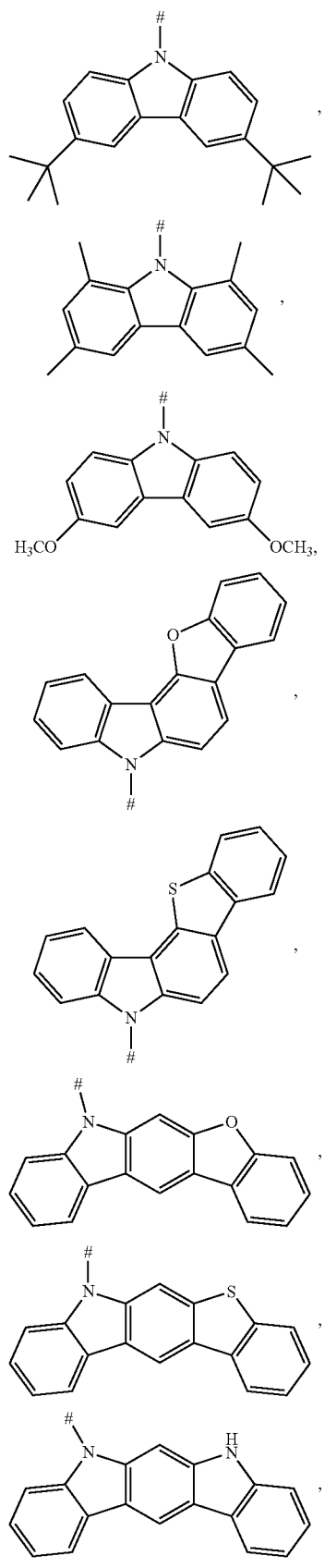
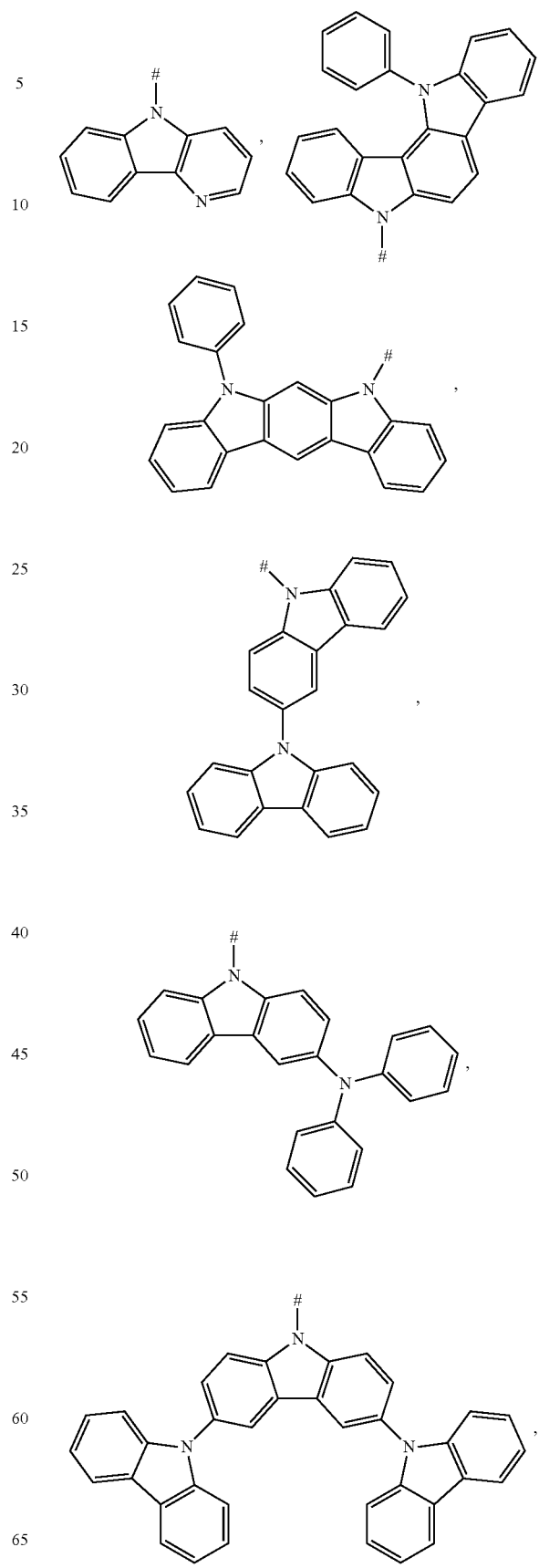

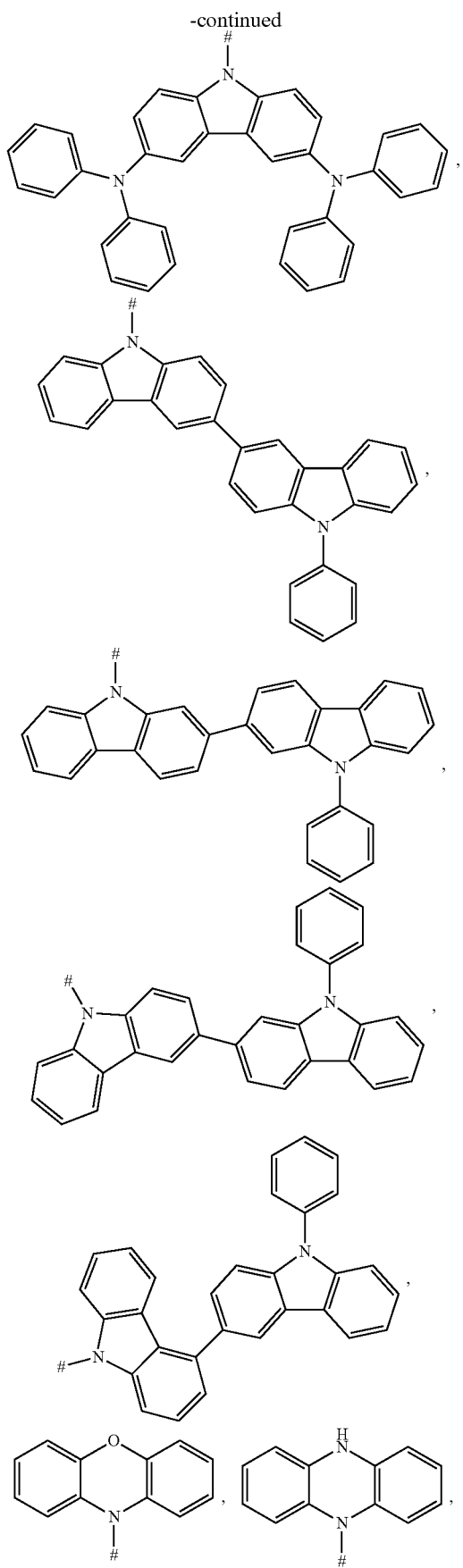
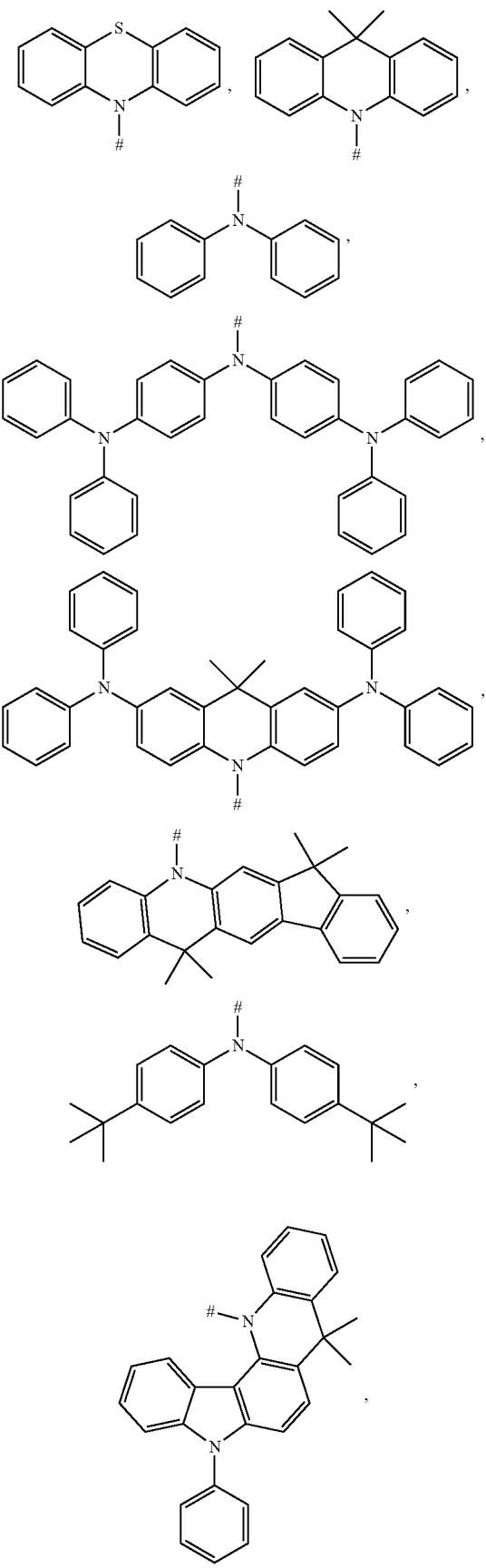

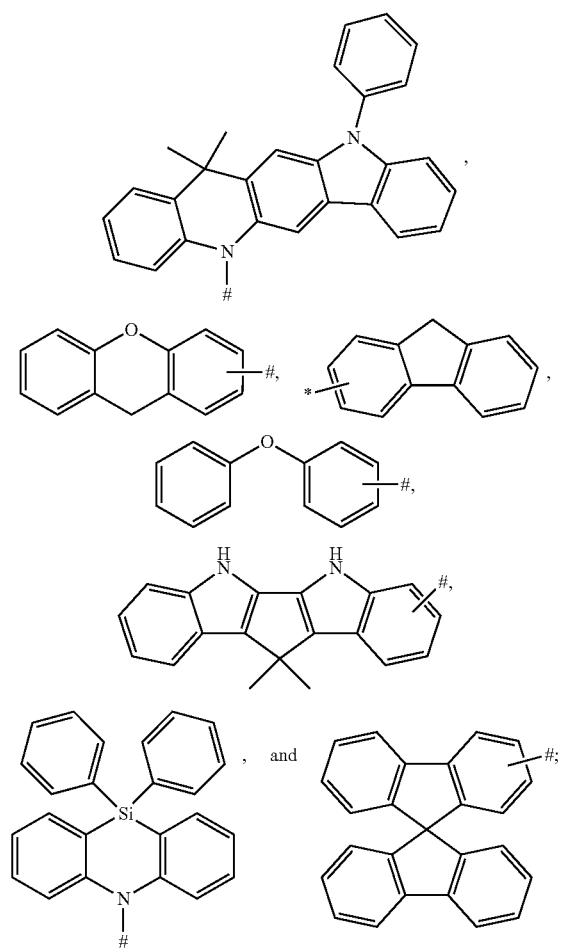
wherein, # represents a linking site of a group.
11. The azulene ring-containing compound according to claim 3, wherein the azulene ring-containing compound is a compound represented by any one of the following structures;
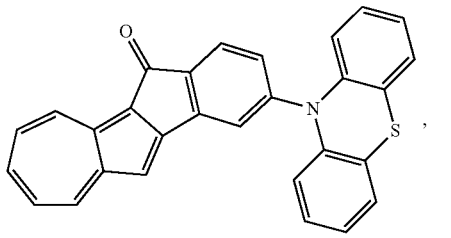
M1
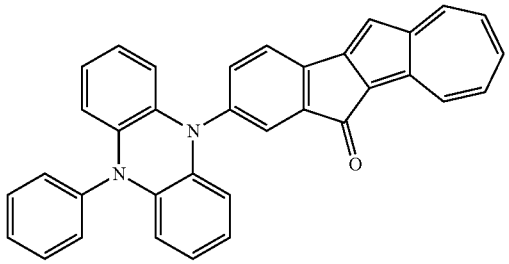
M2
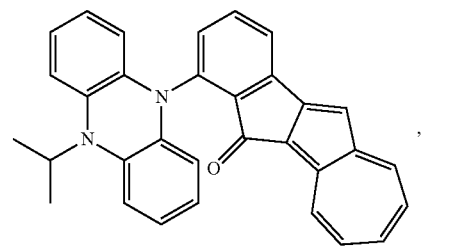
M3
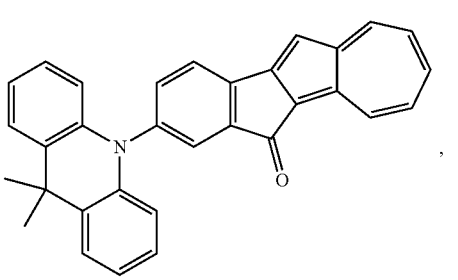
M4
M5
M6
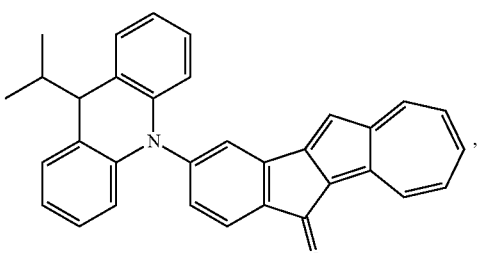
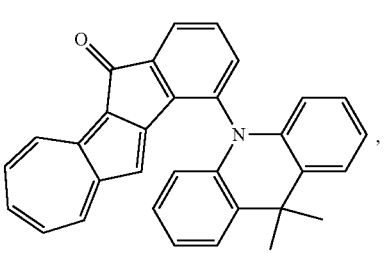
M7
M8

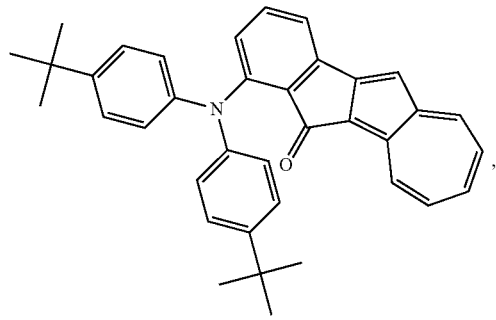
M9
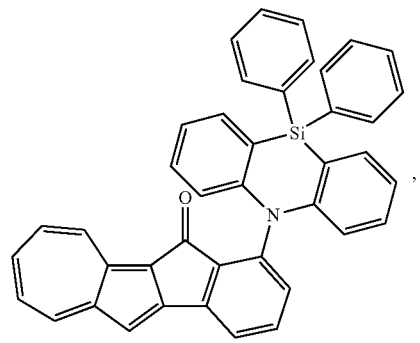
M10
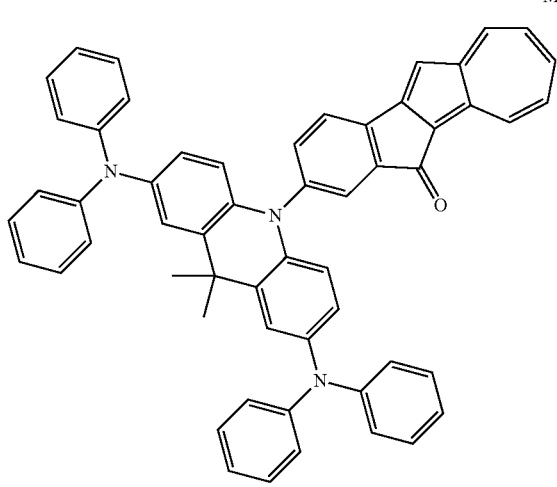
M11
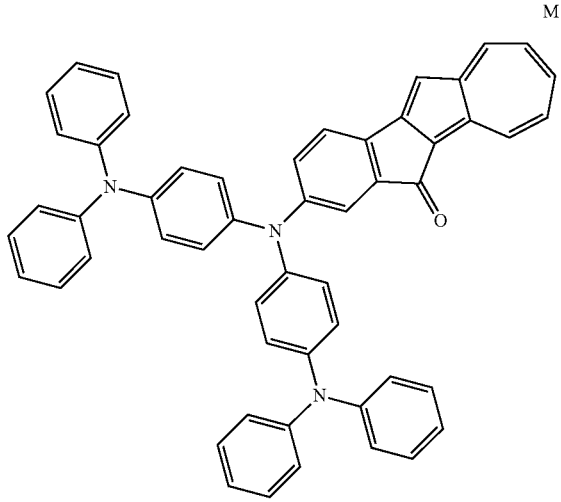
M12
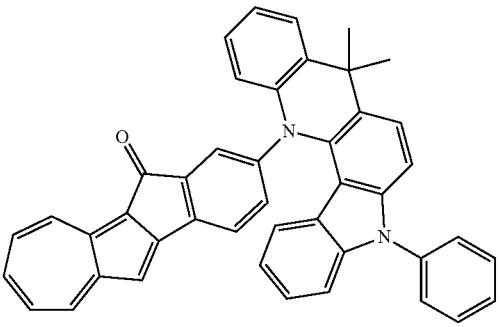
M13
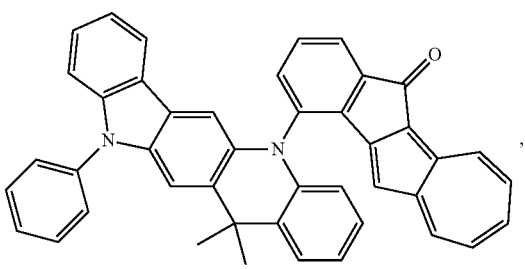
M14
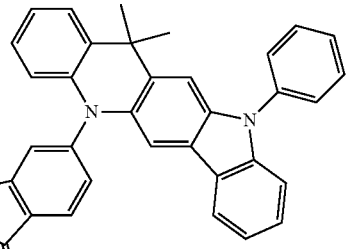
M15
, and
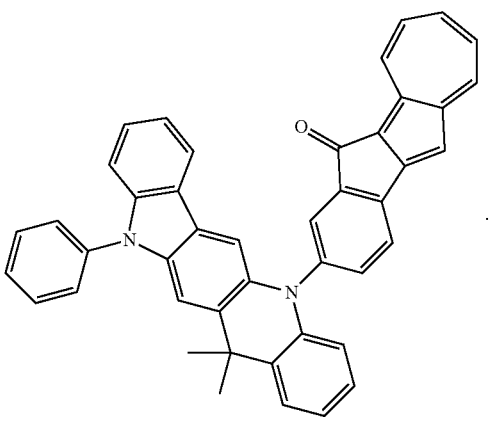
M16
.
12. The azulene ring-containing compound according to claim 4, wherein the azulene ring-containing compound is a compound represented by any one of the following structures:

-continued
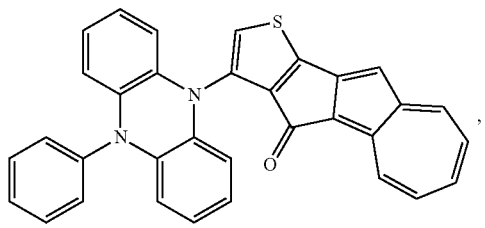
M17
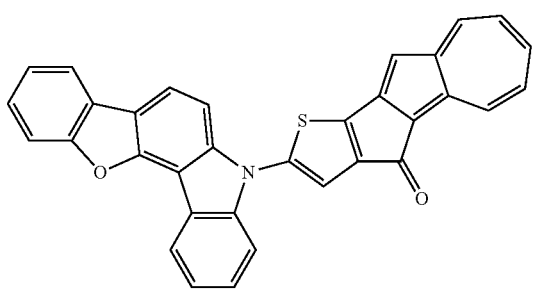
M18
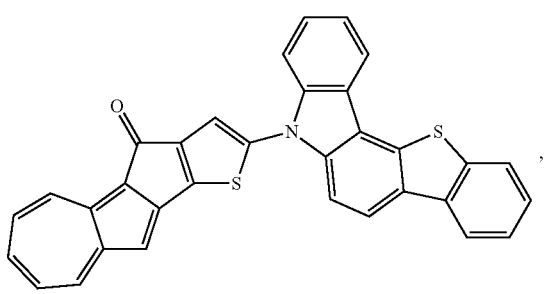
M19
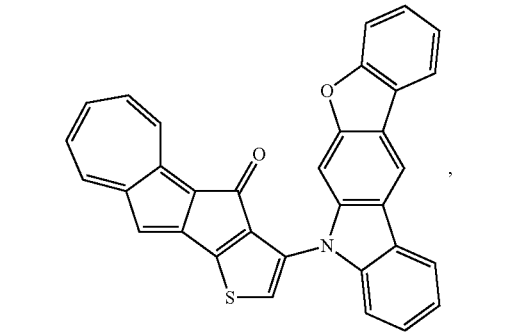
M20
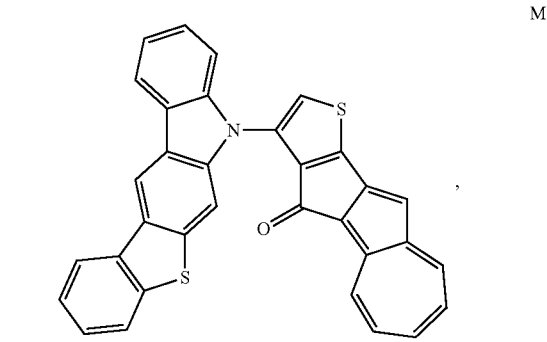
M21
M22
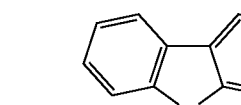
M23
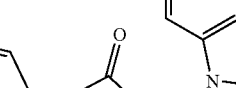
M24
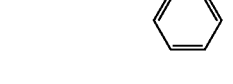
M25

-continued
M26 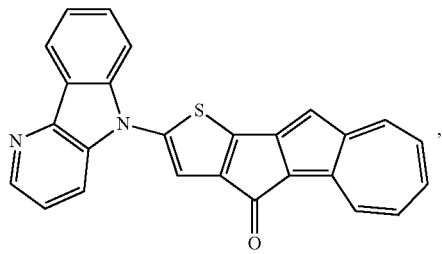
M27 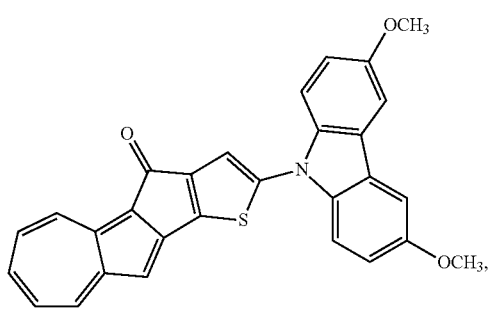
M28 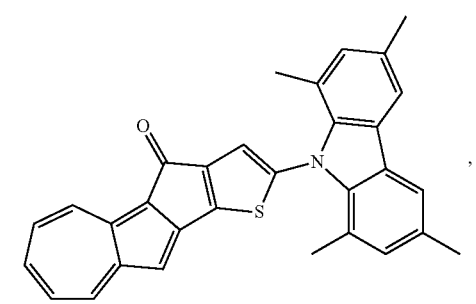
M29 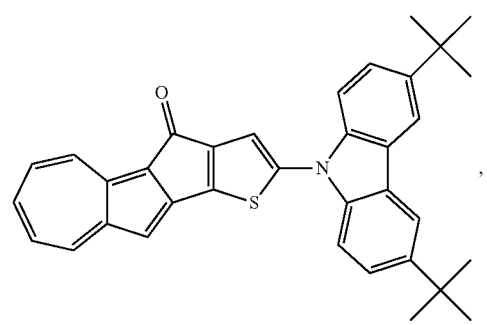
M30 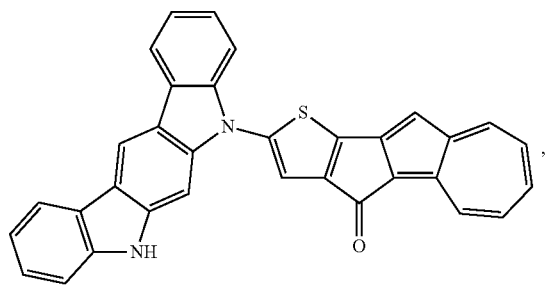
-continued
M31 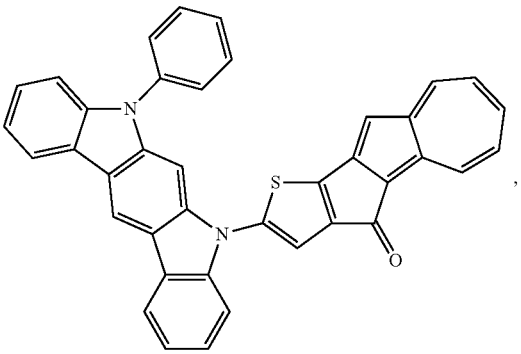
M32 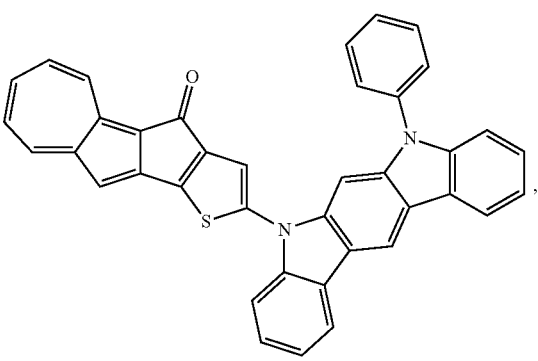
M33 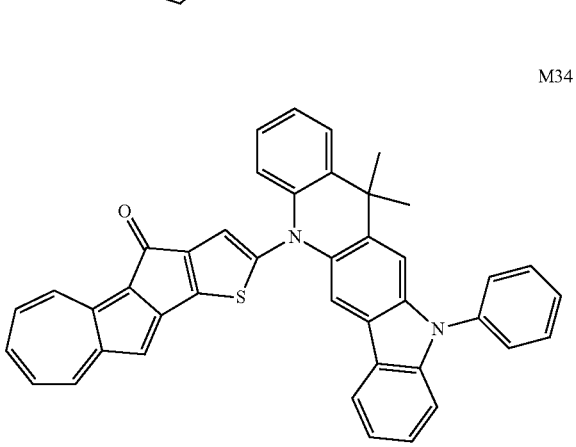
M34 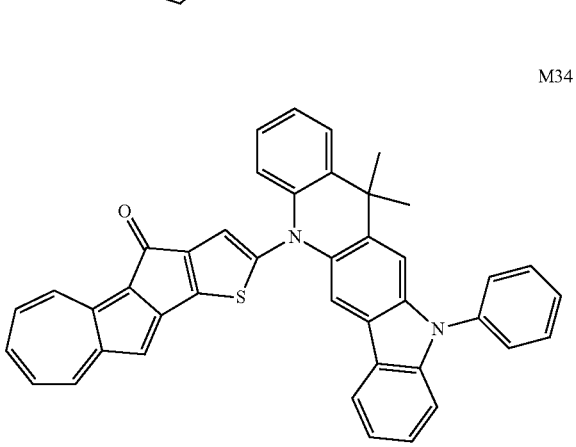
13. The azulene ring-containing compound according to claim 5, wherein the azulene ring-containing compound is a compound represented by any one of the following structures:

M35
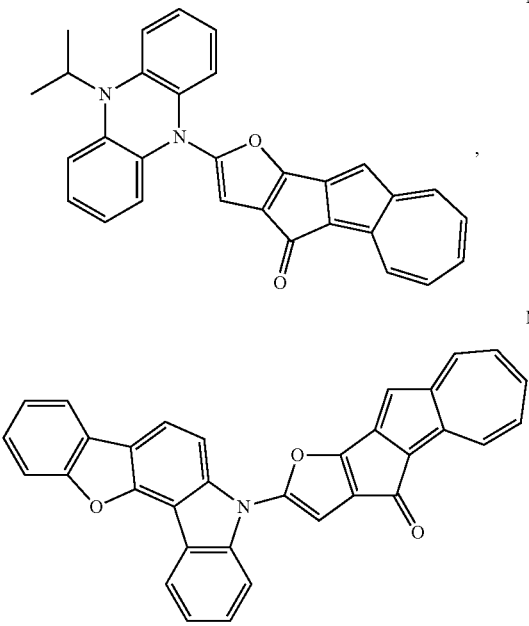,
M40
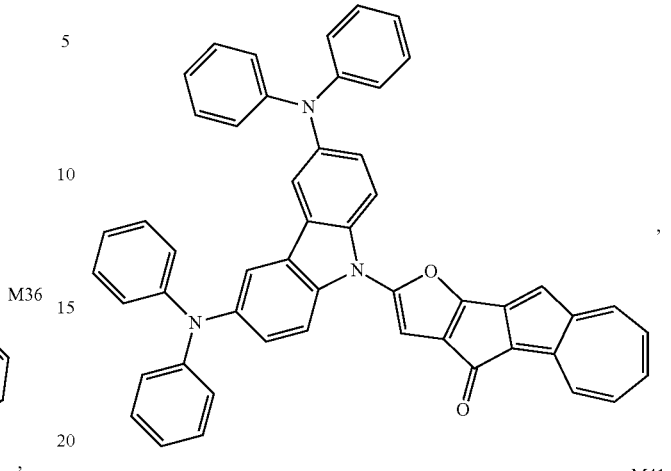,
M36
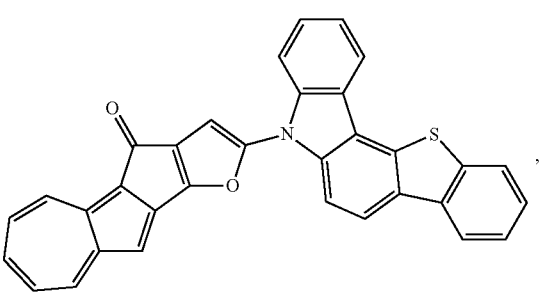,
M41
M37
M42
M38
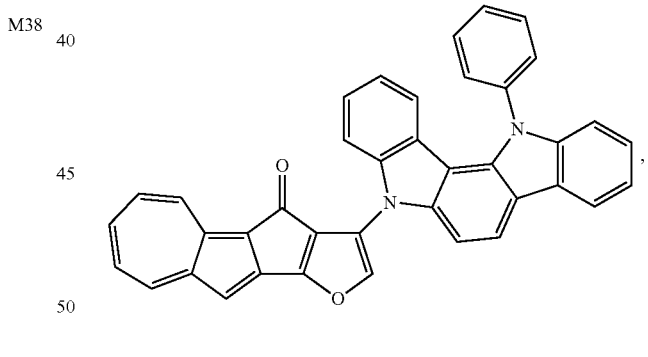,
M39
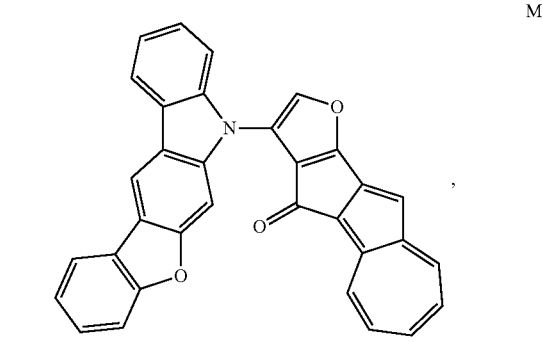,
M43
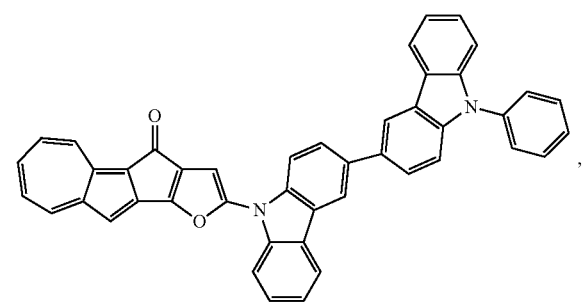, M44
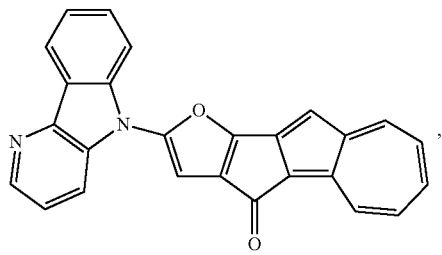
M45
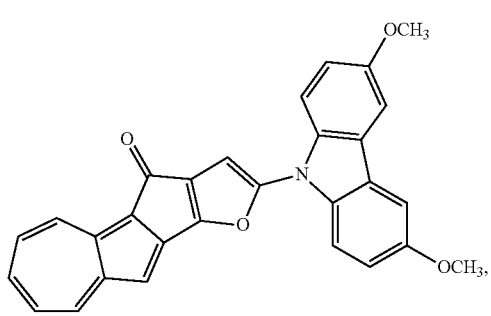
M46
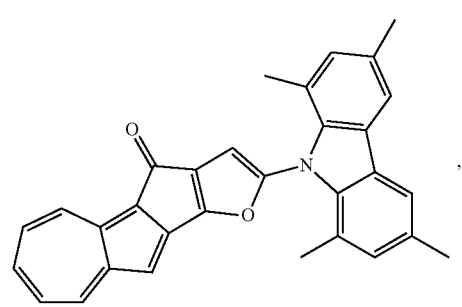
M47
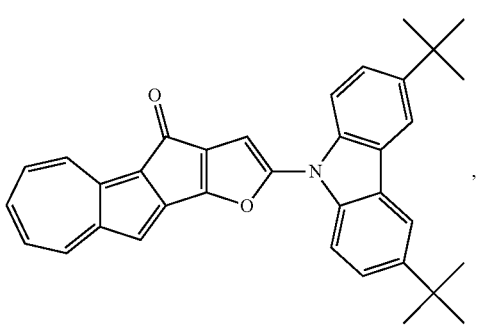
M48
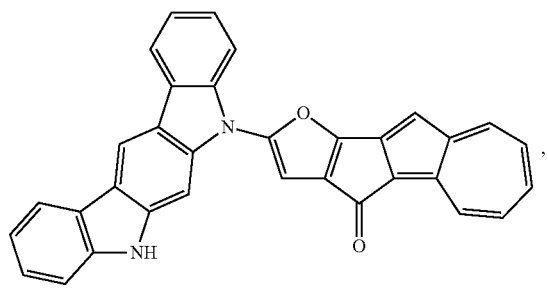
M49
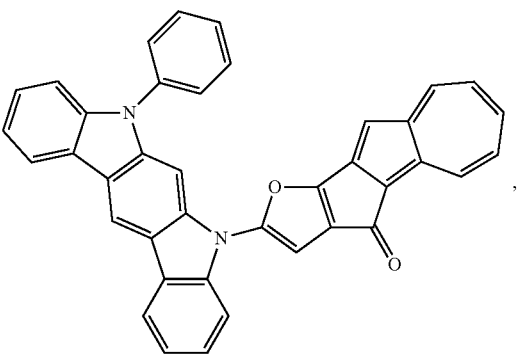
M50
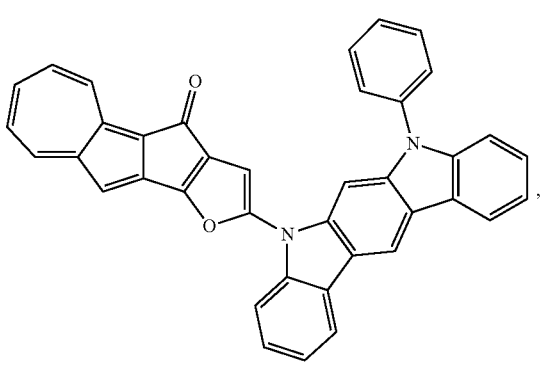
M51
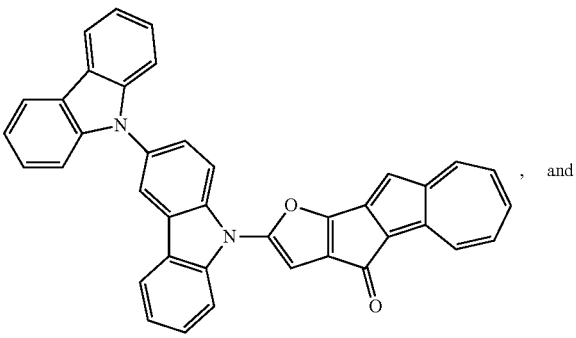
, and
M52
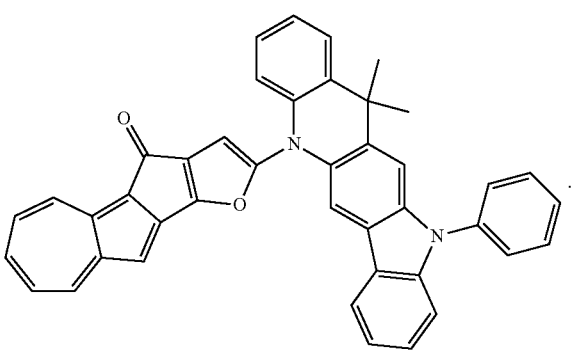
14. The azulene ring-containing compound according to claim 6, wherein the azulene ring-containing compound is a compound represented by any one of the following structures:

M53 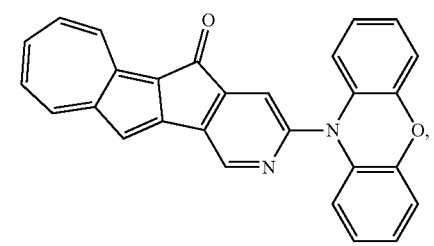
M54 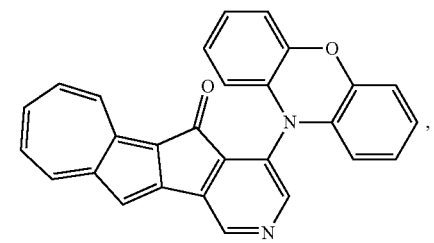
M55 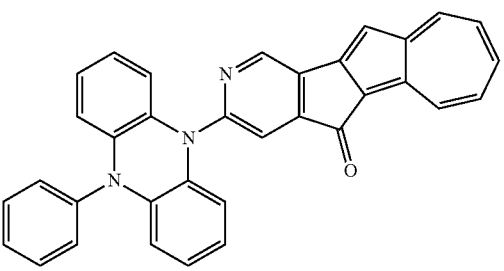
M56 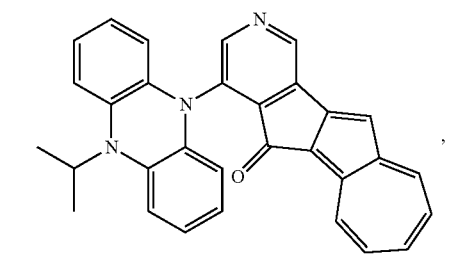
M57 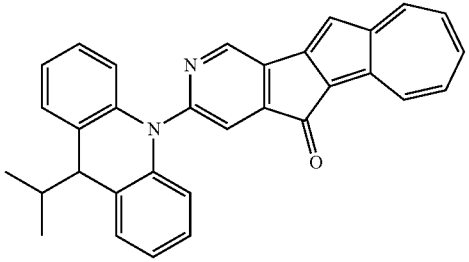
M58 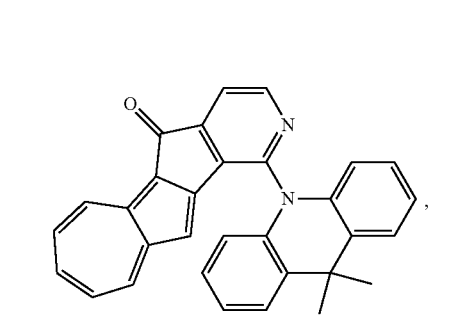
M59 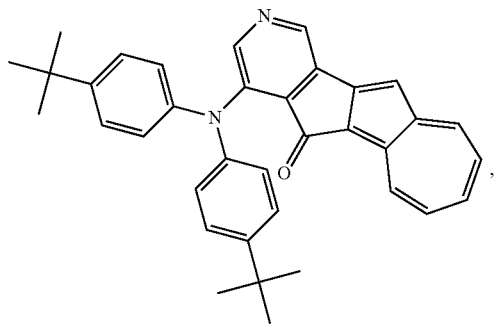
M60 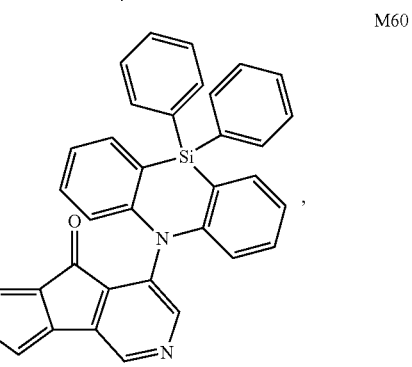
M61 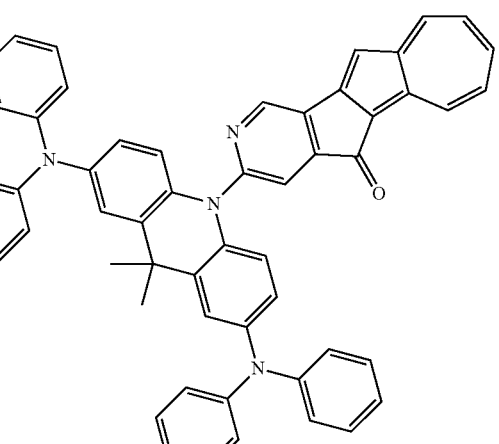
M62 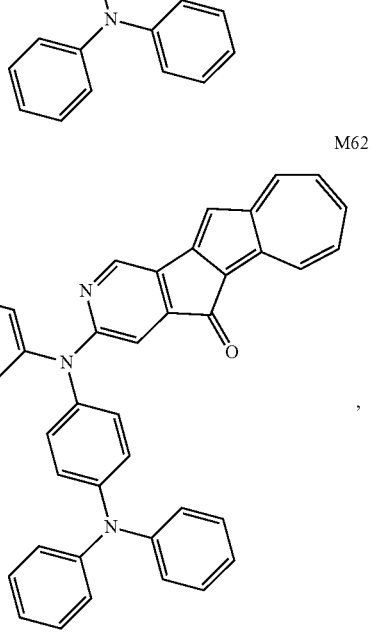

-continued

M63

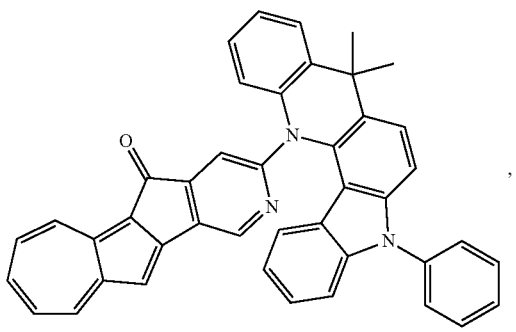

,

M64

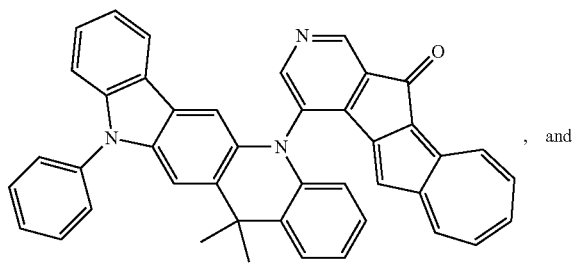

, and

M65

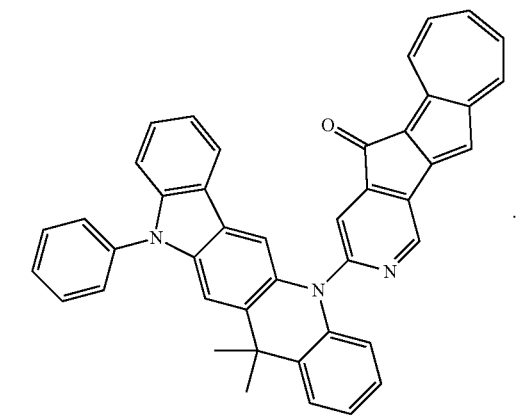

.

15. The azulene ring-containing compound according to claim 1, wherein the azulene ring-containing compound has an energy level difference $\Delta E_{st}=E_{S1}-E_{T1} \leq 0.3$ eV between the lowest singlet state energy level $S_1$ and the lowest triplet state energy level $T_1$.

16. An organic photoelectric device, wherein the organic photoelectric device includes an anode, a cathode, and one or more organic thin film layers located between the anode and the cathode;

and at least one of the organic thin film layers contains the azulene ring-containing compound according to claim 1.

17. The organic optoelectronic device according to claim 16, wherein the organic thin film layer includes at least one light-emitting layer; and the light-emitting layer includes a host material and a guest material, and the host material or the guest material of the light-emitting layer includes the azulene ring-containing compound according to claim 1.

18. The organic optoelectronic device according to claim 17, wherein the organic thin film layer further comprises one or a combination of at least two of a hole injection layer, a hole transport layer, an electron blocking layer, a hole blocking layer, an electron transport layer, and an electron injection layer.

19. The organic optoelectronic device according to claim 17, wherein the organic optoelectronic device comprises an anode, a hole injection layer, a hole transport layer, an electron blocking layer, a light-emitting layer, a hole blocking layer, an electron transport layer, an electron injection layer and a cathode which are sequentially laminated; and the guest material of the light-emitting layer is selected from one or a combination of at least two of the azulene ring-containing compound according to claim 1.

* * * * *